United States Patent
Rothman et al.

(10) Patent No.: US 7,150,971 B2
(45) Date of Patent: Dec. 19, 2006

(54) MEMBRANE-RESIDENT STEROID RECEPTORS AND METHODS OF USE THEREOF

(75) Inventors: Joel H. Rothman, Santa Barbara, CA (US); Erin Newman-Smith, Santa Barbara, CA (US); Gina Broitman-Maduro, Santa Barbara, CA (US)

(73) Assignee: The Regents of the University of California, Oakland, CA (US)

( * ) Notice: Subject to any disclaimer, the term of this patent is extended or adjusted under 35 U.S.C. 154(b) by 626 days.

(21) Appl. No.: 10/153,398

(22) Filed: May 21, 2002

(65) Prior Publication Data

US 2003/0108987 A1   Jun. 12, 2003

Related U.S. Application Data

(60) Provisional application No. 60/292,553, filed on May 21, 2001.

(51) Int. Cl.
  *G01N 33/53* (2006.01)
  *A61K 39/00* (2006.01)
  *C07K 1/00* (2006.01)
(52) U.S. Cl. ................... 435/7.1; 435/7.2; 435/7.8; 424/265.1; 530/350
(58) Field of Classification Search ................ None
  See application file for complete search history.

(56) References Cited

U.S. PATENT DOCUMENTS

| | | | |
|---|---|---|---|
| 5,597,705 A | 1/1997 | Evans et al. | |
| 5,599,904 A | 2/1997 | Evans et al. | |
| 5,639,876 A | 6/1997 | Tripp et al. | |
| 5,846,711 A | 12/1998 | Moore et al. | |
| 5,866,686 A | 2/1999 | Moore et al. | |
| 5,962,256 A | 10/1999 | Moore et al. | |
| 6,358,712 B1 | 3/2002 | Jarrell et al. | |
| 6,465,627 B1 | 10/2002 | McCabe et al. | |

OTHER PUBLICATIONS

Mickle JE et al. Genotype-phenotype relationships in cystic fibrosis. Med Clin North Am. May 2000;84(3):597-607.*
Voet et al. Biochemistry. 1990. John Wiley & Sons, Inc. pp. 126-128 and 228-234.*
Yan et al., Two-amino acid molecular switch in an epithelial morphogen that regulates binding to two distinct receptors. Science 290: 523-527, 2000.*
Skolnick et al. 2000. Trends in Biotech. 18:34-39.*
Bork 2000. Genome Research 10:398-400.*
Doerks et al. 1998. Trends in Genetics 14:248-250.*
Smith et al. 1997. Nature Biotechnology 15:1222-1223.*
Brenner. 1999. Trends in Genetics. 15:132-133.*
Bork et al. 1996 Trends in Genetics. 12:425-427.*
Nagy et al. 2004. Trends in Biochemical Science. 29:317-324.*
Wu et al. 2002. Parasitology Int. 51:155-161.*
Carmi et al. (1998) The nuclear hormone receptor SEX-1 is an X-chromosome signal that determines nematode sex. *Nature* 396: 168-73.
Kostrouchova et al. (1998) CHR3: a *Caenorhabditis elegans* orphan nuclear hormone receptor required for proper epidermal development and molting. *Development* 125(9): 1617-1626.
Kostrouchova et al. (2001) Nuclear hormone receptor CHR3 is a critical regulator of all four larval molts of the nematode *Caenorhabditis elegans*. *PNAS USA* 98(13): 7360-7365.
Much et al. (2000) The fax-1 nuclear hormone receptor regulates axon pathfinding and neurotransmitter expression *Development* 127(4) 703-712.
Siddiqui et al. (2000) A cDNA encoding a nuclear hormone receptor of the steroid/thyroid hormone-receptor superfamily from the human parasitic nematode *Strongyloides stercoralis*. *Parasitol Res* 86(1): 24-29.
Sluder et al. (1997) The *Caenorhabditis elegans* orphan nuclear hormone receptor gene nhr-2 functions in early embryonic development. *Dev Biol* 184(2): 303-319.
Snow and Larsen (2000) Structure and expression of daf-12: a nuclear hormone receptor with three isoforms that are involved in development and aging in *Caenorhabditis elegans*. *Biochim Biophys Acta* 1494(1-2): 104-116.
Zhou and Walthall (1998) UNC-55, an orphan nuclear hormone receptor, orchestrates synaptic specificity among two classes of motor neurons in *Caenorhabditis elegans*. *J Neurosci* 18(24): 10438-10444.

* cited by examiner

*Primary Examiner*—Lorraine Spector
*Assistant Examiner*—Shulamith H. Shafer
(74) *Attorney, Agent, or Firm*—David J. Aston; Peters, Verny, Jones, Schmitt & Aston, LLP

(57) ABSTRACT

This invention pertains to the discovery that DPR-1 encodes a putative nuclear hormone receptor (NHR) that, based on gene reporter studies, is expressed in the endoderm throughout the life of the worm. NHR family members are transcriptional regulators that are activated when bound to their small lipophilic ligands such as steroids. While some NHRs are localized to the nucleus, others are cytoplasmic in the absence of ligand and translocate to the nucleus upon ligand binding. Once in the nucleus, they bind target sequences and regulate gene expression.

21 Claims, 20 Drawing Sheets

E16

E20

Comma

```
                            SEQUENCE LISTING

<160> NUMBER OF SEQ ID NOS: 18

<210> SEQ ID NO 1
<211> LENGTH: 53
<212> TYPE: PRT
<213> ORGANISM: Caenorhabditis elegans

<400> SEQUENCE: 1

Cys Leu Val Cys Gly Asp Glu Ala Ser Gly Cys His Tyr Gly Val Val
1               5                   10                  15

Thr Cys Gly Ser Cys Lys Val Phe Phe Lys Arg Ala Val Glu Gly Gln
            20                  25                  30

His Asn Tyr Leu Cys Ala Gly Arg Asn Asp Cys Ile Ile Asp Lys Ile
        35                  40                  45

Arg Arg Lys Asn Cys
    50

<210> SEQ ID NO 2
<211> LENGTH: 54
<212> TYPE: PRT
<213> ORGANISM: Caenorhabditis elegans

<400> SEQUENCE: 2

Cys Ser Val Cys Asn Phe Ser Ser Leu Ile Ala Pro His Phe Gly Gly
1               5                   10                  15

Leu Val Cys Ser Ala Cys Ala Ser Phe Phe Arg Arg Thr Val Ala Leu
            20                  25                  30

Asn Ile His Tyr Leu Cys Lys Lys Asp Asn Gln Cys Lys Gly Met Arg
        35                  40                  45

Lys Asn Cys Arg Ala Cys
    50

<210> SEQ ID NO 3
<211> LENGTH: 53
<212> TYPE: PRT
<213> ORGANISM: Caenorhabditis elegans

<400> SEQUENCE: 3
```

-continued

Cys Leu Val Cys Gly Ile Glu Lys Gly Thr Leu His Phe Gly Ser Val
1               5                   10                  15

Val Cys Met Ala Cys Ala Ser Phe Phe Arg Arg Thr Val Ser Phe His
                20                  25                  30

Ile Arg Phe Leu Cys Arg Tyr Ser Asn Asn Cys Gln Ile Ser Gln Asp
                35                  40                  45

Leu Arg Phe Ile Cys
            50

<210> SEQ ID NO 4
<211> LENGTH: 53
<212> TYPE: PRT
<213> ORGANISM: Homo sapiens

<400> SEQUENCE: 4

Cys Leu Val Cys Gly Asp Ile Ala Ser Gly Tyr His Tyr Gly Val Ala
1               5                   10                  15

Ser Cys Glu Ala Cys Lys Ala Phe Phe Lys Arg Thr Ile Gln Gly Asn
                20                  25                  30

Ile Glu Tyr Ser Cys Pro Ala Thr Asn Glu Cys Glu Ile Thr Lys Arg
                35                  40                  45

Arg Arg Lys Ser Cys
            50

<210> SEQ ID NO 5
<211> LENGTH: 53
<212> TYPE: PRT
<213> ORGANISM: Homo sapiens

<400> SEQUENCE: 5

Cys Leu Ile Cys Gly Asp Glu Ala Ser Gly Cys His Tyr Gly Val Leu
1               5                   10                  15

Thr Cys Gly Ser Cys Lys Val Phe Phe Lys Arg Ala Met Glu Gly Gln
                20                  25                  30

His Asn Tyr Leu Cys Ala Gly Arg Asn Asp Cys Ile Val Asp Lys Ile
                35                  40                  45

Arg Arg Lys Asn Cys
            50

<210> SEQ ID NO 6
<211> LENGTH: 53
<212> TYPE: PRT
<213> ORGANISM: Homo sapiens

<400> SEQUENCE: 6

Cys Leu Val Cys Gly Asp Val Ala Ser Gly Tyr His Tyr Gly Val Ala
1               5                   10                  15

Ser Cys Glu Ala Cys Lys Ala Phe Phe Lys Arg Thr Leu Gln Gly Ser
                20                  25                  30

Ile Glu Tyr Ser Cys Pro Ala Ser Asn Glu Cys Glu Ile Thr Lys Arg
                35                  40                  45

Arg Arg Lys Ala Cys
            50

<210> SEQ ID NO 7
<211> LENGTH: 54
<212> TYPE: PRT
<213> ORGANISM: Homo sapiens

<400> SEQUENCE: 7

Cys Leu Val Cys Thr Ile Thr Glu Asn Val Arg Phe His Phe Gly Ser
1               5                   10                  15

Thr Thr Cys Leu Ala Cys Ala Ser Phe Phe Arg Arg Thr Val Ser Leu
            20                  25                  30

Lys Ile Gln Tyr Val Cys Lys Gln Ser Asn Asn Cys Ile Val Ser His
        35                  40                  45

Ala Val Arg Ser Gly Cys
            50

<210> SEQ ID NO 8
<211> LENGTH: 49
<212> TYPE: PRT
<213> ORGANISM: Caenorhabditis elegans

<400> SEQUENCE: 8

Thr Leu Asn Arg Leu Ala Gly Lys Gln Met Ile Gln Val Val Lys Trp
1               5                   10                  15

Ala Lys Val Leu Pro Gly Phe Lys Asn Leu Pro Leu Glu Asp Gln Ile
            20                  25                  30

Thr Leu Ile Gln Tyr Ser Trp Met Cys Leu Ser Ser Phe Ala Leu Ser
        35                  40                  45

Trp

<210> SEQ ID NO 9
<211> LENGTH: 49
<212> TYPE: PRT
<213> ORGANISM: Caenorhabditis elegans

<400> SEQUENCE: 9

Glu Leu Phe Glu Ile Val Ser Tyr Gln Ser Lys Val Ala Ala Glu Thr
1               5                   10                  15

Cys Arg Thr Cys Pro Gly Val Asp Leu Leu Asp Asn Arg Asp Ile Leu
            20                  25                  30

Ile Leu Arg Lys Tyr Phe Gln Phe Ser Asn Ile Trp Ile Glu Ser Thr
        35                  40                  45

Trp

<210> SEQ ID NO 10
<211> LENGTH: 49
<212> TYPE: PRT
<213> ORGANISM: Caenorhabditis elegans

<400> SEQUENCE: 10

Asn Phe Leu Glu Thr Lys His Arg Thr Asp Gln Phe Ala Leu Asp Ile
1               5                   10                  15

Cys Thr Met Cys Pro Gly Thr Asp Leu Leu Glu Asn Pro Asp Phe Glu
            20                  25                  30

Val Leu Tyr Lys Tyr Cys Ser Phe Ser Ser Leu Trp Met Asp Leu Ser
        35                  40                  45

Trp

<210> SEQ ID NO 11
<211> LENGTH: 49
<212> TYPE: PRT
<213> ORGANISM: Homo sapiens

<400> SEQUENCE: 11

Thr Leu Cys Asp Leu Ala Asp Arg Glu Leu Val Val Ile Ile Gly Trp

```
                    1               5                  10                 15
Ala Lys His Ile Pro Gly Phe Ser Ser Leu Ser Leu Gly Asp Gln Met
            20                  25                  30

Ser Leu Ile Gln Ser Ala Trp Met Glu Ile Leu Ile Leu Gly Ile Val
            35                  40                  45

Tyr

<210> SEQ ID NO 12
<211> LENGTH: 49
<212> TYPE: PRT
<213> ORGANISM: Homo sapiens

<400> SEQUENCE: 12

Ser Leu Asn Gln Leu Gly Glu Arg Gln Leu Leu Ser Val Val Lys Trp
1               5                  10                 15

Ser Lys Ser Leu Pro Gly Phe Arg Asn Leu His Ile Asp Asp Gln Ile
            20                  25                  30

Thr Leu Ile Gln Tyr Ser Trp Met Ser Leu Met Val Phe Gly Leu Gly
            35                  40                  45

Trp

<210> SEQ ID NO 13
<211> LENGTH: 49
<212> TYPE: PRT
<213> ORGANISM: Homo sapiens

<400> SEQUENCE: 13

Thr Leu Cys Asp Leu Phe Asp Arg Glu Ile Val Val Thr Ile Ser Trp
1               5                  10                 15

Ala Lys Ser Ile Pro Gly Phe Ser Ser Leu Ser Leu Ser Asp Gln Met
            20                  25                  30

Ser Val Leu Gln Ser Val Trp Met Glu Val Leu Val Leu Gly Val Ala
            35                  40                  45

Gln

<210> SEQ ID NO 14
<211> LENGTH: 49
<212> TYPE: PRT
<213> ORGANISM: Homo sapiens

<400> SEQUENCE: 14

Thr Leu Gly Gln Leu Asn Gln Gln Asn His Val Glu Ser Glu Phe Ile
1               5                  10                 15

Cys Lys Asn Cys Pro Gly Thr Asp Leu Ile Ser Thr Glu Asp Lys Met
            20                  25                  30

Ile Leu Ile Gln Tyr Val Lys Phe Ala Asn Leu Trp Leu Asp Ala Leu
            35                  40                  45

Trp

<210> SEQ ID NO 15
<211> LENGTH: 356
<212> TYPE: PRT
<213> ORGANISM: Caenorhabditis elegans

<400> SEQUENCE: 15

Met Asp Gln Ser Asn Ser Asp Gln Thr Asn Glu Val Ala Arg Thr Cys
1               5                  10                 15

Leu Val Cys Thr Ile Thr Glu Asn Val Arg Phe His Phe Gly Ser Thr
```

```
                  20                  25                  30
Thr Cys Leu Ala Cys Ala Ser Phe Phe Arg Arg Thr Val Ser Leu Lys
             35                  40                  45

Ile Gln Tyr Val Cys Lys Gln Ser Asn Asn Cys Ile Val Ser His Ala
         50                  55                  60

Val Arg Ser Gly Cys Arg Ser Cys Arg Phe Gln Asn Cys Leu Lys Ser
 65                  70                  75                  80

Gly Met Lys Thr Asn Met Val Arg Gly Lys Arg Asp Ile Asn Lys Val
                 85                  90                  95

Pro Lys Tyr Ile Arg Glu Ser Met Gln Gln Gly Asp Asn Met Thr Val
            100                 105                 110

Arg Asn Tyr Thr Thr Ser Thr Leu Glu Thr Leu His Gly Phe Pro Lys
            115                 120                 125

Gln Glu Glu Leu Glu Leu Pro Val Val Lys Glu Asp Ala Pro Asn Leu
        130                 135                 140

Leu Ile Val Ser Pro Asp Gln Leu Leu Asp Tyr Tyr Leu Asp Leu Asn
145                 150                 155                 160

Glu Lys Glu Pro Leu Pro Leu Ser Lys Ile His Leu Asn Thr Leu Gly
                165                 170                 175

Gln Leu Asn Gln Gln Asn His Val Glu Ser Glu Phe Ile Cys Lys Asn
            180                 185                 190

Cys Pro Gly Thr Asp Leu Ile Ser Thr Glu Asp Lys Met Ile Leu Ile
        195                 200                 205

Gln Tyr Val Lys Phe Ala Asn Leu Trp Leu Asp Ala Leu Trp Asp Glu
    210                 215                 220

Leu His Ala Lys Asp Lys Gln Asp Lys Gln Asn Leu Val His Cys Gly
225                 230                 235                 240

Glu Phe Ala Asp Tyr Asp Arg Leu Phe Ser Thr Phe Ile Ser Asn Leu
                245                 250                 255

Tyr Glu Ser Val Gly Gln Phe Leu Cys Asn Leu Asn Leu Asp Ile Val
            260                 265                 270

Glu Tyr Ser Ala Leu Lys Ser Phe Val Ile Trp Lys Leu Gly Val Val
        275                 280                 285

Asp Phe Ser Ile Thr Leu Lys Ile Val Ala Gln Glu His Tyr Leu Gly
    290                 295                 300

Val Ser Ala Ala Leu Ile Glu Tyr Tyr Lys Thr Glu Lys Asn Met Glu
305                 310                 315                 320

Glu Met Glu Ile Ala Val Arg Phe Ala Asp Leu Thr Leu Leu Leu Gly
                325                 330                 335

Pro Ile Phe Asn Ser Tyr Lys Glu Met Val Asn Leu Tyr Glu Glu Ile
            340                 345                 350

Arg Thr Phe Val
        355

<210> SEQ ID NO 16
<211> LENGTH: 1611
<212> TYPE: DNA
<213> ORGANISM: Caenorhabditis elegans
<220> FEATURE:
<221> NAME/KEY: CDS
<222> LOCATION: (438)..(1508)

<400> SEQUENCE: 16
cattcgggat atttaaaaac tatcaactga aaaatttgca agaaatcagt aataaacaaa      60
acgatagttg acactttttt gctgcgcctg ctggcctgca gatttgatgt ttcacaatgt     120
```

-continued

```
cttttccgat tctcacagaa ctttggtgca gatctatctc cgaaagcgcg tgagtcccca    180
agaatcttgg tggtctttta gatgatatca agaaagttat gtcctgttcc cacagtgaca    240
tgaccctaca gtatgcacaa tctcgagaat ctttctaaaa tattcaaaaa aaggtccgaa    300
attatgctat tctccagttc acactttttt atttttaaaa aaactctccg aatggagata    360
aaaggagggc ccatggggag acgtcaacgc agattttgc tgtacacttc atattttgaa     420
actacagaaa ttgaaaa atg gat caa tct aat tct gat caa acc aac gaa       470
                   Met Asp Gln Ser Asn Ser Asp Gln Thr Asn Glu
                    1               5                   10 gta gcc cga aca tgt ctg gtt tgt act atc aca gaa aat gtt cga ttc      518
Val Ala Arg Thr Cys Leu Val Cys Thr Ile Thr Glu Asn Val Arg Phe
            15                  20                  25 cac ttc ggt tcg act acg tgc ttg gct tgt gct tca ttt ttc cgc agg      566
His Phe Gly Ser Thr Thr Cys Leu Ala Cys Ala Ser Phe Phe Arg Arg
        30                  35                  40 act gtt tct ctg aaa att caa tat gtg tgt aaa cag tca aat aat tgc      614
Thr Val Ser Leu Lys Ile Gln Tyr Val Cys Lys Gln Ser Asn Asn Cys
    45                  50                  55 att gtt tcg cat gct gta aga agt gga tgc cgg tcg tgc cgt ttt cag      662
Ile Val Ser His Ala Val Arg Ser Gly Cys Arg Ser Cys Arg Phe Gln
60                  65                  70                  75 aat tgt ctg aaa tct gga atg aaa act aat atg gtt cga ggg aaa cga      710
Asn Cys Leu Lys Ser Gly Met Lys Thr Asn Met Val Arg Gly Lys Arg
        80                  85                  90 gac atc aat aaa gtt ccc aag tac atc cga gag tcg atg caa caa gga      758
Asp Ile Asn Lys Val Pro Lys Tyr Ile Arg Glu Ser Met Gln Gln Gly
    95                  100                 105 gat aac atg act gtt cga aac tac aca aca tcc aca ttg gaa act ctt      806
Asp Asn Met Thr Val Arg Asn Tyr Thr Thr Ser Thr Leu Glu Thr Leu
        110                 115                 120 cat ggc ttt cca aaa caa gaa gag tta gag cta ccg gtt gtc aag gaa      854
His Gly Phe Pro Lys Gln Glu Glu Leu Glu Leu Pro Val Val Lys Glu
    125                 130                 135 gat gct ccg aac ctg ttg ata gtt tcg ccc gat caa ctt tta gat tac      902
Asp Ala Pro Asn Leu Leu Ile Val Ser Pro Asp Gln Leu Leu Asp Tyr
140                 145                 150                 155 tat tta gac ctg aat gaa aaa gag ccg ctc cca ttg agc aag atc cat      950
Tyr Leu Asp Leu Asn Glu Lys Glu Pro Leu Pro Leu Ser Lys Ile His
            160                 165                 170 ctc aac acg ctt ggt caa cta aat caa caa aac cac gtg gaa tca gaa      998
Leu Asn Thr Leu Gly Gln Leu Asn Gln Gln Asn His Val Glu Ser Glu
        175                 180                 185 ttt att tgt aaa aac tgc cca gga act gat tta ata agt aca gaa gat     1046
Phe Ile Cys Lys Asn Cys Pro Gly Thr Asp Leu Ile Ser Thr Glu Asp
    190                 195                 200 aaa atg ata tta att caa tac gtg aaa ttt gca aat ctt tgg ctg gac     1094
Lys Met Ile Leu Ile Gln Tyr Val Lys Phe Ala Asn Leu Trp Leu Asp
205                 210                 215 gcc tta tgg gat gaa ctt cat gcg aaa gac aaa caa gac aaa cag aat     1142
Ala Leu Trp Asp Glu Leu His Ala Lys Asp Lys Gln Asp Lys Gln Asn
220                 225                 230                 235 tta gtc cac tgt gga gaa ttt gct gac tac gac aga ctc ttc tct aca     1190
Leu Val His Cys Gly Glu Phe Ala Asp Tyr Asp Arg Leu Phe Ser Thr
            240                 245                 250 ttc att tca aac ctt tac gaa agc gtt ggt cag ttt ctg tgt aat cta     1238
Phe Ile Ser Asn Leu Tyr Glu Ser Val Gly Gln Phe Leu Cys Asn Leu
        255                 260                 265
```

-continued

```
aat ctt gac att gtt gaa tat tcc gcc ctc aaa tcg ttt gtc atc tgg      1286
Asn Leu Asp Ile Val Glu Tyr Ser Ala Leu Lys Ser Phe Val Ile Trp
            270                 275                 280 aaa ctt gga gtt gta gat ttt agt ata acc ctg aaa att gtt gcc caa      1334
Lys Leu Gly Val Val Asp Phe Ser Ile Thr Leu Lys Ile Val Ala Gln
285                 290                 295 gag cac tat ctt gga gtt tcc gct gca tta atc gaa tat tat aaa act      1382
Glu His Tyr Leu Gly Val Ser Ala Ala Leu Ile Glu Tyr Tyr Lys Thr
300                 305                 310                 315 gaa aaa aat atg gaa gag atg gaa att gca gtt aga ttt gct gat ttg      1430
Glu Lys Asn Met Glu Glu Met Glu Ile Ala Val Arg Phe Ala Asp Leu
            320                 325                 330 aca ctt tta ctc gga cca att ttt aac agc tac aag gaa atg gtg aac      1478
Thr Leu Leu Leu Gly Pro Ile Phe Asn Ser Tyr Lys Glu Met Val Asn
                335                 340                 345 ctt tac gaa gag att cga aca ttt gtt tga aaactcccaa tagttcgata        1528
Leu Tyr Glu Glu Ile Arg Thr Phe Val
            350                 355 aaacatttca attttgtac agaataagtc gtaaaaagta attttgttc aatatactgt      1588 aaatgaagtt tcaaattttt aaa                                            1611
```

<210> SEQ ID NO 17
<211> LENGTH: 356
<212> TYPE: PRT
<213> ORGANISM: Caenorhabditis elegans

<400> SEQUENCE: 17

```
Met Asp Gln Ser Asn Ser Asp Gln Thr Asn Glu Val Ala Arg Thr Cys
1               5                   10                  15

Leu Val Cys Thr Ile Thr Glu Asn Val Arg Phe His Phe Gly Ser Thr
                20                  25                  30

Thr Cys Leu Ala Cys Ala Ser Phe Phe Arg Arg Thr Val Ser Leu Lys
            35                  40                  45

Ile Gln Tyr Val Cys Lys Gln Ser Asn Asn Cys Ile Val Ser His Ala
        50                  55                  60

Val Arg Ser Gly Cys Arg Ser Cys Arg Phe Gln Asn Cys Leu Lys Ser
65                  70                  75                  80

Gly Met Lys Thr Asn Met Val Arg Gly Lys Arg Asp Ile Asn Lys Val
                85                  90                  95

Pro Lys Tyr Ile Arg Glu Ser Met Gln Gln Gly Asp Asn Met Thr Val
            100                 105                 110

Arg Asn Tyr Thr Thr Ser Thr Leu Glu Thr Leu His Gly Phe Pro Lys
        115                 120                 125

Gln Glu Glu Leu Glu Leu Pro Val Val Lys Glu Asp Ala Pro Asn Leu
    130                 135                 140

Leu Ile Val Ser Pro Asp Gln Leu Leu Asp Tyr Tyr Leu Asp Leu Asn
145                 150                 155                 160

Glu Lys Glu Pro Leu Pro Leu Ser Lys Ile His Leu Asn Thr Leu Gly
                165                 170                 175

Gln Leu Asn Gln Gln Asn His Val Glu Ser Glu Phe Ile Cys Lys Asn
            180                 185                 190

Cys Pro Gly Thr Asp Leu Ile Ser Thr Glu Asp Lys Met Ile Leu Ile
        195                 200                 205

Gln Tyr Val Lys Phe Ala Asn Leu Trp Leu Asp Ala Leu Trp Asp Glu
    210                 215                 220

Leu His Ala Lys Asp Lys Gln Asp Lys Gln Asn Leu Val His Cys Gly
```

```
                    225                 230                 235                 240

Glu Phe Ala Asp Tyr Asp Arg Leu Phe Ser Thr Phe Ile Ser Asn Leu
                        245                 250                 255

Tyr Glu Ser Val Gly Gln Phe Leu Cys Asn Leu Asn Leu Asp Ile Val
                    260                 265                 270

Glu Tyr Ser Ala Leu Lys Ser Phe Val Ile Trp Lys Leu Gly Val Val
                275                 280                 285

Asp Phe Ser Ile Thr Leu Lys Ile Val Ala Gln Glu His Tyr Leu Gly
            290                 295                 300

Val Ser Ala Ala Leu Ile Glu Tyr Tyr Lys Thr Glu Lys Asn Met Glu
        305                 310                 315                 320

Glu Met Glu Ile Ala Val Arg Phe Ala Asp Leu Thr Leu Leu Leu Gly
                        325                 330                 335

Pro Ile Phe Asn Ser Tyr Lys Glu Met Val Asn Leu Tyr Glu Glu Ile
                    340                 345                 350

Arg Thr Phe Val
                355

<210> SEQ ID NO 18
        <211> LENGTH: 2527
        <212> TYPE: DNA
        <213> ORGANISM: Caenorhabditis elegans

<400> SEQUENCE: 18
cattcgggat atttaaaaac tatcaactga aaaatttgca agaaatcagt aataaacaaa      60
acgatagttg acacttttt gctgcgcctg ctggcctgca gatttgatgt ttcacaatgt     120
cttttccgat tctcacagaa ctttggtgca gatctatctc cgaaagcgcg tgagtcccca     180
agaatcttgg tggtctttta gatgatatca agaaagttat gtcctgttcc cacagtgaca     240
tgaccctaca gtatgcacaa tctcgagaat ctttctaaaa tattcaaaaa aggtccgaa      300 attatgctat tctccagttc acacttttt atttttaaa aaactctccg aatggagata     360
aaaggagggc ccatggggag acgtcaacgc agatttttgc tgtacacttc atattttgaa     420
actacagaaa ttgaaaaatg gatcaatcta attctggtga gttttactct taataattat     480
ggtaaaaaat ttgacataat cttctattat atttttagaa tctataaatt tcgtggcaac     540
tttcagatca accaacgaa gtagcccgaa catgtctggt ttgtactatc acagaaaatg     600
ttcgattcca cttcggttcg actacgtgct tggcttgtgc ttcatttttc cgcaggactg     660
tttctctgaa aattcaatat gtgtgtaaac agtcaaataa ttgcattgtt tcgcatggta     720
cggtaacctc agaaaacata aaaatggttt tatacaaaag agggtacaat aaaaattctg     780
gtgatgaatt acgcgcgaaa tgtcgctaaa tgtatggaaa taagtttgt gacgtcatat     840 agtcatggcg gcattacttg aataacccca ttaccactag ttgaaaattt ttacttttt     900 cgaagaactg tcaaatttga attattcata aggaaagctt cataaggaac ttgagctgct     960
atctagtttt aaagtaccat ttattttcag ctgtaagaag tggatgccgg tcgtgccgtt    1020
ttcagaattg tctgaaatct ggaatgaaaa ctaatagtat gttttcaaat aacttaaaat    1080
aaaatctcaa tactttattt tagtggttcg agggaaacga acatcaata aagttcccaa    1140 gtacatccga gagtcgatgc aacaaggaga taacatgact gttcgaagta agctcttta    1200 cggttttata aaaataatta ttttctttgt tagactacac aacatccaca ttggaaactc    1260
ttcatggctt tccaaaacaa gaagagttag agctaccggt tgtcaaggaa gatgctccga    1320
acctgttgat agtttcgccc gatcaacttt tagattacta tttagacctg aatgaaaaag    1380
```

-continued

```
agccgctccc attgagcaag atccatctca acacgcttgg tcaactaaat caacaaaacc    1440
acgtggaatc agaatttatt tgtaaaaact gcccaggaac tgatttaata agtacagaag    1500
ataaaatgat attaattcaa tacgtgaaat ttgcaaatct ttggctggac gccttatggg    1560
atgaacttca tgcgaaagac aaacaagaca aacagaattt agtccactgt ggagaatttg    1620
ctgactacga caggttcgat tgaaattacc tttatattca cagtagatat tttaacattc    1680
tcaataatct cactgaattt ataaaaaagg gtttaaaacc ttaaatatga agatcttttt    1740
cttagcgaga ttcccaaagc cttttttgagt gccgttgaca attatgaaaa ttatgaagtt    1800
aacttatttc gaatttttca aaataaatct tgaaaaagct tgctagaatt atcttccgct    1860
aatgaaagaa tcacgtgaaa tttatgcctg attacatatt acactaatta catactaatt    1920
gtaaacacat ataattagtc taattacaaa accagaaaaa tttggtaata ttttaccgat    1980
ttctagtcaa ttcaagtatt tcagactctt ctctacattc atttcaaacc tttacgaaag    2040
cgttggtcag tttctgtgta atctaaatct tgacattgtt gaatattccg ccctcaaatc    2100
gtttgtcatc tggaaacttg gagttgtaga ttttagtata accctgaaaa ttgttgccca    2160
agagcactat cttggagttt ccgctgcatt aatcgaatat tataaagtag gtgggcaatg    2220
attaatgtca gtgataaatc taattttcag actgaaaaaa atatggaaga gatgaaatt    2280
gcagttagat ttgctgattt gacactttta ctcggaccaa tttttgtgag tttcaaagca    2340
tataatctta attatctaaa agtgttacag aacagctaca aggaaatggt gaacctttac    2400
gaagagattc gaacatttgt ttgaaaactc ccaatagttc gataaaacat ttcaattttt    2460
gtacagaata agtcgtaaaa agtaattttt gttcaatata ctgtaaatga agtttcaaat    2520
ttttaaa                                                              2527
```

MEMBRANE-RESIDENT STEROID RECEPTORS AND METHODS OF USE THEREOF

CROSS-REFERENCE TO RELATED APPLICATIONS

This application claims benefit of and priority to U.S. Ser. No. 60/292,553, filed on May 21, 2001, which is incorporated herein by reference in its entirety for all purposes.

STATEMENT AS TO RIGHTS TO INVENTIONS MADE UNDER FEDERALLY SPONSORED RESEARCH AND DEVELOPMENT

This work was supported by National Institutes of Health National Institute of Child Health and Human Development grant number HD37487, a National Institutes of Health National Institute of General Medicine NRSA fellowship, and a March of Dimes Birth Defects Foundation grant. The Government of the United States of America may have certain rights in this invention.

FIELD OF THE INVENTION

This invention pertains to the field of nuclear hormone receptors. In particular, this invention pertains to the identification of a nuclear hormone receptor that, under certain circumstances, is also resident at or in the cell membrane.

BACKGROUND OF THE INVENTION

Nuclear hormone receptors are ligand-activated transcription factors that regulate gene expression by interacting with specific DNA sequences typically upstream of their target genes. A two-step mechanism of action has been was proposed for these receptors based upon the observation of an inactive and an active state of the receptors. The first step involves activation through binding of the hormone; the second step consists of receptor binding to DNA and regulation of transcription.

After being bound by or interacting with its cognate ligand (e.g. a hormone), the nuclear hormone receptor typically binds to a hormone response element (HRE). A hormone response element is a specific DNA sequence that a hormone receptor recognizes with markedly increased affinity. The hormone receptor element typically contains two consensus hexameric half-sites. The identity of a response element generally resides in three features: the sequence of the base pairs in the half-site, the number of base pairs between the half-sites and the relative orientation of the two half-sites. Thus each receptor protein dimer that binds the DNA typically recognizes the sequence, spacing and orientation of the half-sites within their response element.

Binding of the response element by the nuclear receptor typically results in the up- or down-regulation of one or more genes under control of the response element. It is believed that, prior to this invention, this was the only way that nuclear hormone receptors, and specifically, steroid receptors functioned.

SUMMARY OF THE INVENTION

This invention pertains to the discovery that DPR-1 (formerly known as END-2) a putative nuclear hormone receptor (NHR) that, based on gene reporter studies, is expressed in the endoderm throughout the life of the worm *C. elegans*. NHR family members are transcriptional regulators that are activated when bound to their small lipophilic ligands such as steroids. While some NHRs are localized to the nucleus, others are cytoplasmic in the absence of ligand and translocate to the nucleus upon ligand binding. Once in the nucleus, they bind target sequences and regulate gene expression.

We have found that while DPR-1 is present in the nucleus during early development, unexpectedly, it appears to localize to the plasma membrane under certain conditions later in development. DPR-1 antibody reveals nuclear expression of the protein in posterior cells of early embryos (pre-bean stage), consistent with RNA in situ analysis. However, by the bean stage, DPR-1 antigen relocalizes to the plasma membranes of developing gut cells. This membrane association continues through to hatching. Our preliminary biochemical results further indicate that DPR-1 partially associates with the membrane fraction obtained from both early and late embryos based on western blot analysis of embryonic extracts.

We found that in larvae, DPR-1 antigen is either primarily cytoplasmic (and nuclear-excluded) or is localized to the membrane, depending on the preparation examined. The variable localization of DPR-1 to the cytoplasm or membrane in larvae is attributable to variations in environmental conditions. When *C. elegans* is grown in uncrowded conditions, DPR-1 is present throughout the cytoplasm of gut cells. However, when they are cultured at high density, the protein appears to partition to the membrane. The effect of crowding on DPR-1 localization may be a response to dauer pheromone.

This intriguing localization pattern of DPR-1 is atypical for NHRs and suggests a possible novel mode of action. One postulate is that membrane-associated DPR-1 transduces a signal from the membrane. Such a possibility is consistent with the evidence that a number of steroids can transduce a signal that is independent of transcription, and in some cases the ligands can act without entering the cell. Alternatively, the non-membrane localized form of DPR-1 may function like a typical NHR and localization to the membrane may be a mechanism for sequestering DPR-1, rendering it inactive.

In one embodiment, this invention provides an isolated nuclear hormone receptor where the nuclear hormone receptor comprises a DNA binding domain and a ligand binding domain, the nuclear hormone receptor has at least 20%, preferably at least 30%, more preferably at least 50%, and most preferably at least 60, 80, 90, 95%, or 99% percent amino acid sequence identity with DPR-1 in the DNA binding domain and/or in the ligand binding domain; and is found, in its native state, in a cell nucleus and in a cell membrane. In certain embodiments, the nuclear hormone receptor of has at least 30 percent amino acid sequence identity with DPR-1 in said DNA binding domain and in the ligand binding domain. In particularly preferred embodiments, the nuclear hormone receptor is a nematode nuclear hormone receptor. The nuclear hormone receptor can be encoded by a construct selected from the group consisting of C54C8, ZK381, F41D3, C27C7, ZK1025, C14C6, C17A2, F14A5, C29D10, T15D6, C47F8, C29G2, and E03H4 and/or can be encoded by a gene selected from the group consisting of nhr-20, nhr-53, nhr-16, and nhr-92 and/or a nucleic acid selected from the group consisting of C54C8.1, C41G6.5, F41D3.3, C29G2.5, C47F8.2, E03H4.6, T09E11.2, nhr-20 and nhr-77. In certain embodiments, the nuclear hormone receptor is a mammalian estrogen receptor related (ERR) protein.

This invention also provides an isolated polypeptide comprising an DPR-1 polypeptide encoded by a nucleic acid designated R10D12.2 by the *C. elegans* sequencing consortium, when the nucleic acid comprises: a splice site at position 9544; a start codon at position 9563; and an intron at positions 7675 to 7630. In certain embodiments, the polypeptide is encoded by the nucleic acid when the nucleic acid comprises a C at position 7969 and/or a G at position 8495. Also provided are nucleic acids encoding this polypeptide. Certain polypeptides are encoded by the nucleic acid where the nucleic acid comprises a C at position 7969 and/or a G at position 8495.

In one embodiment this invention provides a polypeptide having the sequence of SEQ ID NO:15.

In still another embodiment, this invention provides an isolated nucleic acid encoding any of the NHR polypeptides described herein and/or a cell comprising such a "heterologous" nucleic acid. In preferred embodiments, the cell is transfected with the NHR (e.g. BTF3 encoding) nucleic acid. Preferred cells include, but are not limited to nematode cells, other invertebrate cells, vertebrate cells, mammalian cells, and human cells. In preferred embodiments, the cell expresses a nuclear hormone receptor (NHR) encoded by the nucleic acid.

This invention also provides a method of producing a nuclear hormone receptor. The method involves providing a vector comprising a promoter (e.g. an inducible promoter, a constitutive promoter, a tissue-specific promoter, etc.) operably linked to a nucleic acid encoding the nuclear hormone receptor as described herein (e.g. a BTF3 nuclear hormone receptor) in a cell whereby said vector expresses said nuclear hormone receptor.

In certain embodiments, this invention provides a method of screening for an agent that alters nematode growth and/or development. The method involves contacting a nuclear hormone receptor of this invention (e.g. a DPR-1 NHR) in a cell with a test agent; and detecting the metabolic activity of said cell wherein a difference in the metabolic activity of said cell as compared to the metabolic activity of a control cell indicates that said test agent is alters development of a nematode. The detecting can comprise measuring the expression level of a gene in the cell, and/or measuring the growth or proliferation of said cell, and/or measuring the activity of a second messenger in the cell.

Also provided is a method of prescreening for an agent that agent that modulates the metabolic activity of a cell and/or that alters growth and/or development of a nematode. The method involves i) contacting a nuclear hormone receptor (NHR) as described herein (e.g. DPR-1) or a nucleic acid encoding said nuclear hormone receptor with a test agent; and ii) detecting specific binding of the test agent to the nuclear hormone receptor and/or to the nucleic acid where specific binding of the test agent to the nucleic acid or to the nuclear hormone receptor indicates that the agent is likely to modulate the metabolic activity of a cell. The method can further involve recording test agents that specifically bind to the nucleic acid or to the nuclear hormone receptor in a database of candidate agents that alter metabolic activity or development of a cell (e.g. a nematode cell). In certain embodiments, the test agent is not an antibody and/or not a protein and/or not a nucleic acid. Preferred test agents include small organic molecules. In certain embodiments, the method involves detecting specific binding of the test agent to the nucleic acid (e.g. via a Northern blot, a Southern blot using DNA derived from an DPR-1 RNA, an array hybridization, an affinity chromatography, and an in situ hybridization, etc.). IN certain embodiments, the method involves detecting specific binding of the test agent to said nuclear hormone receptor polypeptide (e.g. via capillary electrophoresis, a Western blot, mass spectroscopy, ELISA, immunochromatography, a gel-shift assay, a two hybrid assay, an immunohistochemistry, etc.). The test agent can be contacted directly to the nuclear hormone receptor or to the nuclear hormone receptor nucleic acid and/or to a cell containing the nuclear hormone receptor or to the nuclear hormone receptor nucleic acid and/or to a tissue comprising a cell containing the nuclear hormone receptor or to the nuclear hormone receptor nucleic acid, and/or to an animal. The cell can be a cell cultured ex vivo.

This invention provides a method of screening for an agent that modulates dauer formation by nematode. The method involves contacting a nematode with a test agent; and detecting a change in localization of a nuclear hormone receptor, wherein a change in localization indicates that the test agent is a good candidate agent for modulating (inducing or inhibiting) dauer formation by a nematode. IN certain embodiments, the change in localization is a change from localization in the cell nucleus to localization in the cell membrane. In certain embodiments, the change in localization is a change from localization in the cell membrane to the cell nucleus. The localization can be detected by a variety of methods, e.g. by labeling the nuclear receptor hormone. In particularly preferred embodiments, the nuclear hormone receptor is DPR 1.

This invention also provides a method of screening for an agent that inhibits or reverses cyst formation by a nematode. The method involves contacting a DPR-1 nuclear hormone receptor in a cell with a test agent; and detecting the metabolic activity of the cell wherein a difference in the metabolic activity of said cell as compared to the metabolic activity of a control cell indicates that said test agent is likely to inhibit or reverse cyst formation by a nematode. The control cell can be a cell in the absence of the test agent or contacted with the test agent at a different concentration. In certain embodiments, the measuring can comprise measuring the expression level of a gene in the cell and/or measuring the growth and/or proliferation of the cell and/or measuring the activity of a second messenger in the cell. In certain embodiments, the nuclear hormone receptor (e.g. DPR-1) is expressed by a heterologous nucleic acid.

This invention also provides a method of prescreening for an agent that inhibits or reverses cyst formation by a nematode. The method involves i) contacting an DPR-1 nuclear hormone receptor or a nucleic acid encoding an DPR-1 nuclear hormone receptor with a test agent; and ii) detecting specific binding of the test agent to nuclear hormone receptor (e.g. DPR-1) or said nucleic acid where specific binding of the test agent to the nucleic acid or to the nuclear hormone receptor indicates that the test agent is likely to inhibit or reverse cyst formation by a nematode. The contacting can be in a cell (e.g. a nematode cell, a mammalian cell, etc.). In certain embodiments, the method further comprises recording test agents that specifically bind to the nucleic acid or to the nuclear hormone receptor in a database of candidate agents that alter metabolic activity or development of a cell. In certain embodiments, the test agent is not an antibody and/or not a protein, and/or not a nucleic acid. Preferred test agents include, but are not limited to small organic molecules. In certain embodiments, the assay comprises detecting specific binding of said test agent to said nucleic acid (e.g. via a Northern blot, a Southern blot using DNA derived from an DPR-1 RNA, an array hybridization, an affinity chromatography, an in situ hybridization, etc.). In certain embodiments, the assay comprises detecting specific binding of the test agent to the nuclear hormone receptor (e.g. DPR-1) (e.g., via capillary electrophoresis, gel-shift assay, two-hybrid system, a Western blot, mass spectroscopy, ELISA, immunochromatography, immunohistochemistry, etc.). In certain embodiment, the test agent is contacted directly to the nuclear hormone receptor or to the nuclear hormone receptor nucleic acid and/or to a cell containing the nuclear hormone receptor or to the nuclear hormone receptor nucleic acid and/or to a tissue and/or to an animal.

This invention also provides a method of inhibiting or reversing cyst formation by a nematode. The method involves contacting the nematode with an agent that inhibits expression or activity of a DPR-1 receptor (e.g. DPR-1).

Definitions

"Nuclear hormone receptor proteins" refer to a class of ligand activated proteins that, when bound to specific sequences of DNA typically serve as on-off switches for transcription within the cell nucleus. These switches typically control the development and differentiation of various tissues and/or behavioral centers in the brain, as well as the continual regulation of reproductive tissues. The nuclear hormone receptor proteins are typically composed of several domains that are differentially conserved between the various receptors and have different roles: a variable N-terminal region, a conserved DNA binding domain (DBD), a variable hinge region, a conserved ligand binding domain (LBD), and a variable C-terminal region.

A "DNA binding domain" of a nuclear hormone receptor refers to a domain that typically binds to a nucleic acid and, in many cases, thereby targets the receptors to their hormone response elements (HREs). A DNA binding domain, classified as a type-II zinc finger motif, typically has two subdomains, each containing a zinc ion coordinated by four cysteine residues, followed by an alpha-helix. The DBD typically binds as a dimer with each monomer recognizing a six base pair sequence of DNA. The reading helix of each monomer makes sequence specific contacts in the major groove of the DNA at each half-site. These contacts allow the dimer to read the sequence, spacing and orientation of the half-sites within its response element, and thus discriminate between sequences. These proteins exhibit, however, a flexibility in recognizing DNA sequences and also accept a variety of amino-acid substitutions in their reading helix without abolishing binding.

A "ligand biding domain" (LBD) refers to a domain of the nuclear hormone receptor that binds the cognate ligand of that receptor. The LBD can participate in numerous activities including, but not limited to hormone binding, homo- and/or heterodimerization, formation of the heat-shock protein complex and transcriptional activation and repression.

A "membrane-resident steroid receptor" or a "membrane-resident nuclear hormone receptor" refers to a nuclear hormone receptor that, under certain conditions, can also or alternatively be found associated with or bound in a cell membrane (i.e. membrane resident). When the receptor is membrane resident it can provide a signaling function different than that provided when the receptor is found in the cell nucleus.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

The term "specifically binds", as used herein, when referring to a biomolecule (e.g., protein, nucleic acid, antibody, etc.), refers to a binding reaction which is determinative of the presence biomolecule in heterogeneous population of molecules (e.g., proteins and other biologics). Thus, under designated conditions (e.g. immunoassay conditions in the case of an antibody or stringent hybridization conditions in the case of a nucleic acid), the specified ligand or antibody binds to its particular "target" molecule and does not bind in a significant amount to other molecules present in the sample.

The terms "nucleic acid" or "oligonucleotide" or grammatical equivalents herein refer to at least two nucleotides covalently linked together. A nucleic acid of the present invention is preferably single-stranded or double stranded and will generally contain phosphodiester bonds, although in some cases as outlined below, nucleic acid analogs are included that may have alternate backbones, comprising, for example, phosphoramide (Beaucage et al. (1993) *Tetrahedron* 49(10): 1925) and references therein; Letsinger (1970) *J. Org. Chem.* 35:3800; Sprinzl et al. (1977) *Eur. J. Biochem.* 81: 579; Letsinger et al. (1986) *Nucl. Acids Res.* 14: 3487; Sawai et al. (1984) *Chem. Lett.* 805, Letsinger et al. (1988) *J. Am. Chem. Soc.* 110: 4470; and Pauwels et al. (1986) *Chemica Scripta* 26: 1419), phosphorothioate (Mag et al. (1991) *Nucleic Acids Res.* 19:1437; and U.S. Pat. No. 5,644,048), phosphorodithioate (Briu et al. (1989) *J. Am. Chem. Soc.* 111:2321, O-methylphophoroamidite linkages (see Eckstein, *Oligonucleotides and Analogues: A Practical Approach*, Oxford University Press), and peptide nucleic acid backbones and linkages (see Egholm (1992) *J. Am. Chem. Soc.* 114:1895; Meier et al. (1992) *Chem. Int. Ed. Engl.* 31: 1008; Nielsen (1993) *Nature,* 365: 566; Carlsson et al. (1996) *Nature* 380: 207). Other analog nucleic acids include those with positive backbones (Denpcy et al. (1995) *Proc. Natl. Acad. Sci. USA* 92: 6097; non-ionic backbones (U.S. Pat. Nos. 5,386,023, 5,637,684, 5,602,240, 5,216,141 and 4,469,863; Angew. (1991) *Chem. Intl. Ed. English* 30: 423; Letsinger et al. (1988) *J. Am. Chem. Soc.* 110: 4470; Letsinger et al. (1994) *Nucleoside & Nucleotide* 13:1597; Chapters 2 and 3, ASC Symposium Series 580, "Carbohydrate Modifications in Antisense Research", Ed. Y. S. Sanghui and P. Dan Cook; Mesmaeker et al. (1994), *Bioorganic & Medicinal Chem. Lett.* 4: 395; Jeffs et al. (1994) *J. Biomolecular NMR* 34:17; *Tetrahedron Lett.* 37:743 (1996)) and non-ribose backbones, including those described in U.S. Pat. Nos. 5,235,033 and 5,034,506, and Chapters 6 and 7, ASC Symposium Series 580, *Carbohydrate Modifications in Antisense Research*, Ed. Y. S. Sanghui and P. Dan Cook. Nucleic acids containing one or more carbocyclic sugars are also included within the definition of nucleic acids (see Jenkins et al. (1995), *Chem. Soc. Rev.* pp169–176). Several nucleic acid analogs are described in Rawls, C & E News Jun. 2, 1997 page 35. These modifications of the ribose-phosphate backbone may be done to facilitate the addition of additional moieties such as labels, or to increase the stability and half-life of such molecules in physiological environments.

The terms "hybridizing specifically to" and "specific hybridization" and "selectively hybridize to," as used herein refer to the binding, duplexing, or hybridizing of a nucleic acid molecule preferentially to a particular nucleotide sequence under stringent conditions.

The term "stringent conditions" refers to conditions under which a probe will hybridize preferentially to its target subsequence, and to a lesser extent to, or not at all to, other sequences. Stringent hybridization and stringent hybridization wash conditions in the context of nucleic acid hybridization are sequence dependent, and are different under different environmental parameters. An extensive guide to the hybridization of nucleic acids is found in, e.g., Tijssen (1993) *Laboratory Techniques in Biochemistry and Molecular Biology—Hybridization with Nucleic Acid Probes part I, chapt 2, Overview of principles of hybridization and the strategy of nucleic acid probe assays*, Elsevier, N.Y. ( Tijssen ). Generally, highly stringent hybridization and wash conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids which have more than 100 complementary residues on an array or on a filter in a Southern or northern blot is 42° C. using standard hybridization solutions (see, e.g., Sambrook (1989) *Molecular Cloning: A Laboratory Manual* (2nd ed.) Vol. 1–3, Cold Spring Harbor Laboratory, Cold Spring Harbor Press, NY, and detailed discussion, below), with the hybridization being carried out overnight. An example of highly stringent wash conditions is 0.15 M NaCl at 72° C. for about 15 minutes. An example of stringent wash conditions is a 0.2×SSC wash at 65° C. for 15 minutes (see, e.g., Sambrook supra.) for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example of a low stringency wash for a duplex of, e.g., more than 100 nucleotides, is 4× to 6×SSC at 40° C. for 15 minutes.

The phrase "substantially identical," in the context of two nucleic acids or polypeptides, refers to two or more sequences or subsequences that have at least 60%, preferably 80%, most preferably 90–95% nucleotide or amino acid residue identity, when compared and aligned for maximum correspondence, as measured using one of the following sequence comparison algorithms or by visual inspection. Preferably, the substantial identity exists over a region of the sequences that is at least about 50 residues in length, more preferably over a region of at least about 100 residues, and most preferably the sequences are substantially identical over at least about 150 residues. In a most preferred embodiment, the sequences are substantially identical over the entire length of the coding regions.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman (1988) *Proc. Natl. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., supra).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle (1987) *J. Mol. Evol.* 35:351–360. The method used is similar to the method described by Higgins & Sharp (1989) CABIOS 5: 151–153. The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of algorithm that is suitable for determining percent sequence identity and sequence similarity is the BLAST algorithm, which is described in Altschul et al. (1990) *J. Mol. Biol.* 215: 403–410. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) *Proc. Natl. Acad. Sci. USA* 89:10915).

In addition to calculating percent sequence identity, the BLAST algorithm also performs a statistical analysis of the similarity between two sequences (see, e.g., Karlin & Altschul (1993) *Proc. Natl. Acad. Sci. USA*, 90: 5873–5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

The term "test agent" refers to an agent that is to be screened in one or more of the assays described herein. The agent can be virtually any chemical compound. It can exist as a single isolated compound or can be a member of a chemical (e.g. combinatorial) library. In a particularly preferred embodiment, the test agent will be a small organic molecule.

The term "small organic molecule" refers to a molecule of a size comparable to those organic molecules generally used in pharmaceuticals. The term excludes biological macromolecules (e.g., proteins, nucleic acids, etc.). Preferred small organic molecules range in size up to about 5000 Da, more preferably up to 2000 Da, and most preferably up to about 1000 Da.

"Operably linked" when describing the relationship between two DNA or polypeptide sequences, means that they are functionally related to each other. For example, a promoter is operably linked to a coding sequence if it controls the transcription of the sequence; a ribosome binding site is operably linked to a coding sequence if it is positioned so as to permit translation, etc.

The term database refers to a means for recording and retrieving information. In preferred embodiments the database also provides means for sorting and/or searching the stored information. The database can comprise any convenient media including, but not limited to, paper systems, card systems, mechanical systems, electronic systems, optical systems, magnetic systems or combinations thereof. Preferred databases include electronic (e.g. computer-based) databases. Computer systems for use in storage and manipulation of databases are well known to those of skill in the art and include, but are not limited to "personal computer systems", mainframe systems, distributed nodes on an inter- or intra-net, data or databases stored in specialized hardware (e.g. in microchips), and the like.

The term "vector" as used herein refers to a nucleic acid sequence comprising a gene under the control of a promoter (typically a promoter that does not normally control that gene or cDNA in a wild-type cell). The vector typically contains all of the elements necessary for expression of the gene in the host cell. Thus in addition to a promoter the vector typically contains an initiation site and a termination codon. Vectors may also contain elements that aid their replication, manipulation and selection such as origins of replication, multiple cloning sites, selectable markers and the like. The vectors may be circularized and take the form of phagemids, plasmids, cosmids and the like.

An "DPR-1 nuclear hormone receptor" or an "DPR-1 family nuclear hormone receptor" refers to a member of the DPR-1 family of nuclear hormone receptors as described herein. The "DPR-1" receptor can alternatively refer to the *C. elegans* DPR-1 receptor as described herein. The difference in usage will be apparent from context.

The terms "isolated" "purified" or "biologically pure" refer to material which is substantially or essentially free from one or more components that normally accompany it as found in its native state. With respect to nucleic acids and/or polypeptides the term can refer to nucleic acids or polypeptides that are no longer flanked by the sequences typically flanking them in nature. Isolated nucleic acids and polypeptides can thus include polypeptides and nucleic acids that are transfected back into a cell and may therefore be found again in a typical biological mileau.

BRIEF DESCRIPTION OF THE DRAWINGS

(FIGS. 9A, 9B). L1 larvae grown in non-crowded conditions show DPR-1 localization in the cytoplasm. (FIGS. 9C, 9D) In the presence of dauer pheromone, DPR-1 localizes to the membrane.

DETAILED DESCRIPTION

Figure 1:
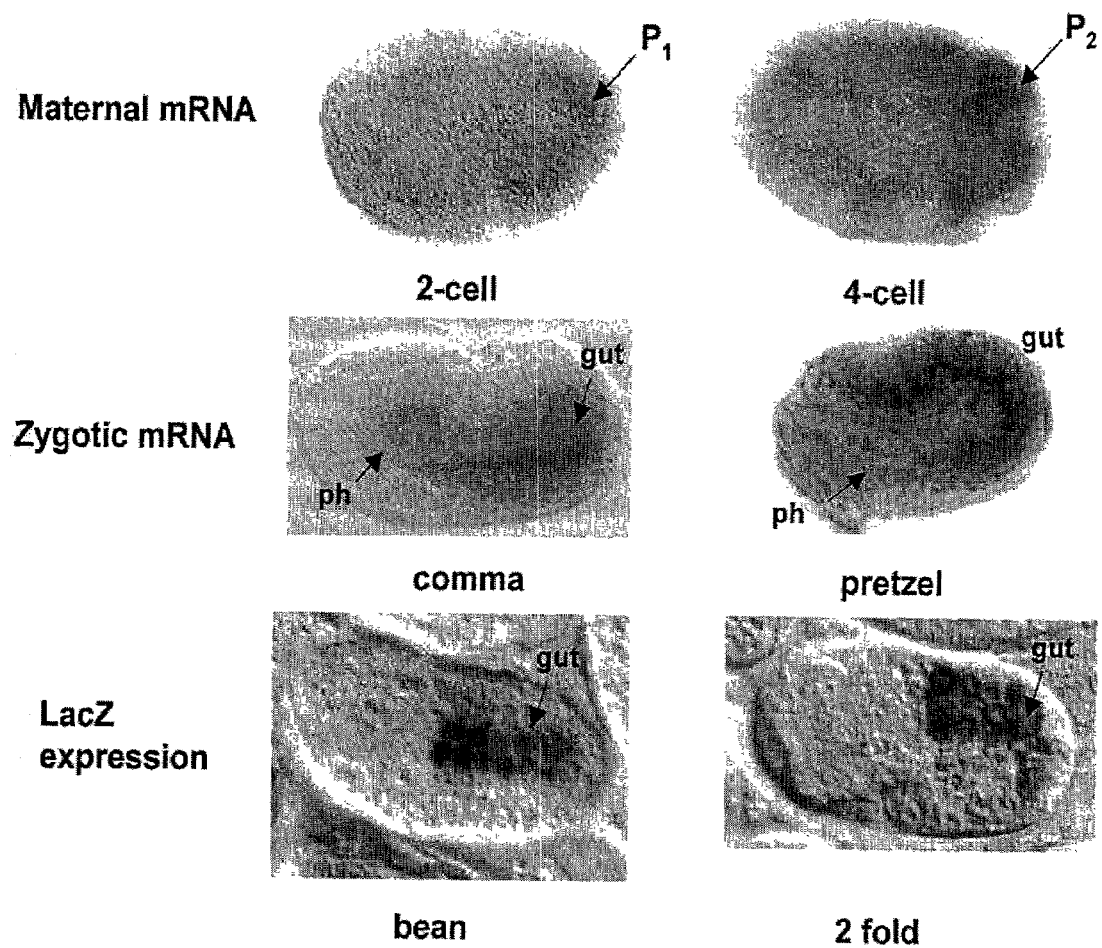
FIG. 1 illustrates DPR-1 expression in embryos.

This invention pertains to the discovery of a novel class of proteins, the DPR-1 family. The DPR-1 protein of the nematode Caenorhabditis elegans (see SEQ ID NO: 17) is a member of the nuclear hormone receptor (NHR) family. Classically, NHRs are localized in the cytoplasm or nucleus of the cell. Steroids or steroid-like molecules, such as retinoids, diffuse across membranes, bind to the appropriate NHR, and cause it to become a transcriptional activator. However, some evidence suggests that steroids may also function at the cell surface. We have found that DPR-1 is primarily localized to the plasma membrane under some naturally occurring circumstances. DPR-1 is the first naturally occurring NHR to be found primarily at the plasma membrane of a cell.

It was a discovery of this invention that DPR-1 moves from the cytoplasm to the plasma membrane in response to a pheromone produce by C. elegans called dauer pheromone. Dauer pheromone is a lipid-like substance that promotes formation of an alternative developmental larval stage, the dauer, which is analogous to certain stages of many pathogenic nematodes that are essential for their infectivity or reproduction. The response of DPR-1 to dauer pheromone suggests that it binds to dauer pheromone and mediates dauer-promoting effects.

The discovery of a nuclear hormone receptor that also resides at the cell membrane reconciles certain previously unexplained observations. Thus, for example, rat pituitary cells release the hormone prolactin within 3 minutes after estrogen treatment (Norfleet et al. (2000) *Faseb J.* 14: 157–165). This response is more rapid than would be possible if new gene transcription were required. Similarly, estrogen is also able to stimulate adenylate cyclase, IP3 generation and GTP-gamma S binding to G proteins when added to membrane preparations of CHO cells transfected with the estrogen receptor (Razandi, et al. (1999) *Mol Endo* 13: 307–319). In addition, steroids that are conjugated with agents such as BSA, and thus cannot enter the cell, can still elicit responses. For example, in frog oocytes, progesterone bound to BSA is capable of stimulating germinal vesicle breakdown (Bandyopahyay et al. (1989) *General and Comparative Endocrinology,* 109: 291–301). However, prior to this invention, no receptor has been found to be primarily localized at the membrane.

As a putative dauer receptor, DPR-1 and its relatives in *C. elegans* and other nematodes, provide a useful target for designing new compounds that are important for control of nematodes in agriculture and medicine. For example, agents that antagonize or activate regulatory points that promote dauer-like stages of pathogenic nematodes will be useful in control of pathogenic nematodes. In addition, it may prove possible to improve biocontrol agents by inducing the infective dauer-like stage in nematodes that kill host insects and other agricultural pests.

The DPR-1 receptor identified herein also has uses in recombinant protein expression. An inducible protein expression system similar to the ecdysone inducible promoter system can be generated to drive expression in response to the dauer pheromone. This would be a useful tool for tight regulation of gene expression.

Because DPR-1 exists in a genetically tractable organism, one can use genetics to determine the components in the signaling pathway at the cell surface. This is helpful in targeting drugs specifically to the membrane function of the NHRs or to the nuclear function of NHRs. This can lead to new therapeutic agents to replace or augment the currently used steroids. Thus, the DPR-1 nuclear hormone receptors provide a novel target for agents that show steroid agonist or antagonist activity.

In preferred embodiments, this invention is useful for developing alternatives to steroid treatment, for developing anti-helminthic agents to use in agriculture and human and veterinary medicine, and for generation of new inducible systems for use in biotechnology.

I. Uses of DPR-1 and DPR-1 Family Members.

DPR-1 is a member of the nuclear hormone receptor family that identifies a new class of NHRs that function at the membrane. DPR-1 defines a family of related proteins in *C. elegans* (see Table 1) and also shows particularly relatedness to proteins in humans, especially the estrogen receptor related genes (ERRs: alpha, beta and gamma), which are similar to DPR-1 throughout the DNA binding domain, and the ligand binding domain. Indeed, the ERRs may be the human equivalent of DPR-1.

Table 1. illustrates the similarities of DPR-1 and other nuclear hormone receptors (NHRs). Alignments are shown for the DNA binding domains and ligand binding domains of DPR-1, C54C8, Y38E10, ERR-beta, ERR-gamma, minerolcorticoid, and human progesterone.

| NHR | Sequence | Seq ID NO: |
|---|---|---|
| DNA Binding Domain: | | |
| DPR-1 (END-2) | CLVCGDEASGCHYGVVT_CGSCKVFFK RAVEGQHNYLCAGRNDCIIDKIRRKNC | 1 |
| C54C8 | CSVCNFSSLIAPHFGGLVCSACASFFR RTVALNTHYLCKKDNQCKGMRKNCRAC | 2 |
| Y38E10 | CLVCGIEKGTLHFGSVV-CMACASFFR RTVSFHIRFLCRYSNNCQISQDLRFIC | 3 |
| ERR-beta | CLVCGDIASGYHYGVAS_CEACKAFFK RTIQGNIEYSCPATNECEITKRRRKSC | 4 |
| ERR-gamma | CLICGDEASGCHYGVLT-CGSCKVFFK RAMEGQHNYLCAGRNDCIVDKIRRKNC | 5 |
| Minerolcorticoid | CLVCGDVASGYHYGVAS-CEACKAFFK RTLQGSIEYSCPASNECEITKRRRKAC | 6 |
| Progesterone | CLVCTITENVRFHFGSTTCLACASFFR RTVSLKIQYVCKQSNNCIVSHAVRSGC | 7 |
| Ligand Binding Domain: | | |
| DPR-1 (END-2) | TLNRLAGKQMIQVVKWAKVLPGFKNLP LEDQITLIQYSWMCLSSFALSW | 8 |
| CS4C8 | ELFEIVSYQSKVAAETCRTCPGVDLLD NRDILILRKYFQFSNIWIESTW | 9 |

-continued

| NHR | Sequence | Seq ID NO: |
|---|---|---|
| Y38E10 | NFLETKHRTDQFALDICTMCPGTDLLE NPDFEVLYKYCSFSSLWMDLSW | 10 |
| ERR-beta | TLCDLADRELVVIIGWAKHIPGFSSLS LGDQMSLIQSAWMEILILGIVY | 11 |
| ERR-gamma | SLNQLGERQLLSVVKWSKSLPGFRNLH IDDQITLIQYSWMSLMVFGLGW | 12 |
| Minerolcorticoid | TLCDLFDREIVVTISWAKSIPGFSSLS LSDQMSVLQSVWMEVLVLGVAQ | 13 |
| Progesterone | TLGQLNQQNHVESEFICKNCPGTDLIS TEDKMILIQYVKFANLWLDALW | 14 |

The classical view of NHRs are as transcription factors that localize to the cytoplasm or nucleus of the cell in the absence of ligand. When the ligand, a small lipophilic molecule, such as steroid or retinoid, is present, it can diffuse across the plasma membrane and bind the NHR. The ligand-activated NHR then translocates to the nucleus (or remains there) and becomes activated, resulting in its ability to regulate transcription of target genes. All steroids, such as cortisone, estrogen, progesterone, etc., as well as many other steroid-like molecules, such as retinoic acid, which are used a pharmacological agents in humans target a nuclear regulatory pathway of this type. These drugs can have many severe side effects.

DPR-1 is localized to the cell membrane when dauer pheromone is present, and without being bound to a particular theory, is believed to interact with second messenger signaling components at the membrane. This novel signaling pathway can be exploited to develop new drugs that target only specific activities of steroids and steroid-like molecules, which may have fewer side effects. DPR-1 is the first example of a NHR that, under normal conditions, is located at the membrane.

C. elegans, as a genetically tractable organism, provides a powerful tool for discovering the components of this novel signaling pathway and the components of the membrane targeting and signaling.

As the potential dauer pheromone receptor, DPR-1 is useful in agriculture and medicine. A large number of nematode species exist that invade and are pathogenic to animals and plants. As the putative dauer pheromone receptor, DPR-1 provides a good target for the development of dauer pheromone agonists and antagonists. Such agents will be useful for promoting or inhibiting dauer-like formation in invasive nematodes, allowing them to be controlled in agricultural or medical situations.

Parasitic nematodes infect and kill destructive insects such as cutworms, which can destroy agricultural crops. Many nematode species (e.g., *Heterorhabditis bacteriophora* and those with similar life cycle habits, such as *Steinernema carpocapsae*) are being cultivated as biocontrol agents for insect pests. Their life cycle includes an L3 infective stage, which is remarkably similar to the dauer stage in *C. elegans*. By manipulating the dauer/L3 infective state such that the dauer/L3 infective pathway is chosen, more effective nematodes, and thus more effective biological controls might be generated.

One way to do this is to generate altered genetic forms of the DPR-1 homologue in the parasitic species that promotes dauer formation. In addition, with the dauer pheromone receptor in hand, dauer pheromone agonists can be generated using well-know screening methods (e.g. screening for changes in metabolic activity induced by test agent interaction with DPR-1, and/or screening for DPR-1 binding agents). Regardless of its mode of action, DPR-1 is responsive to dauer pheromone, and as such, is useful for disrupting the dauer pathway, in these different nematodes.

In addition to the medical and agricultural potential benefits arising from DPR-1, DPR-1 can also be used to generate an inducible promoter system for biotechnological applications. This system would allow researchers to express proteins of interest under the control of DPR-1 and dauer pheromone. For instance, a gene would be placed downstream of a promoter containing several DPR-1 binding sites, and transfected into tissue culture cells along with a construct containing a modified DPR-1 that goes to the nucleus (such as our N-terminal GFP/DPR-1 fusions). On addition of dauer pheromone, DPR-1 could direct transcription of the downstream gene. Because tissue culture cells don't produce dauer pheromone, this system would allow researchers to turn genes on and off easily and without interference from endogenous ligands. A system similar to this using the ecdysone receptor from Drosophila is in use today. The benefits of using DPR-1 is that it can be used in some tissue culture cells that the ecdysone receptor may be expressed in, such as insect cell lines (e.g., S9 cells). In addition, it provides researchers with other options, which may be useful for experiments where it is desirable to express two genes independently.

Another possible biotechnological use for the DPR-1 protein is to use it to target proteins to the membrane. By analyzing DPR-1 localization, the amino acid domain necessary for membrane targeting can be identified. Our current results indicate that the amino terminal portion of the protein is important for its localization. The localization domain could be exploited to generate a system that would allow researchers to target proteins specifically to the membrane in a way that is regulated by ligand (e.g., dauer pheromone). By directing the protein to one location or the other, one can determine the function of the protein in different sub-cellular compartments. Such a system could also be exploited to alter the localization of proteins in response to a regulatory molecule as a way of regulating cellular conditions or physiology. In addition, targeting proteins to the surface of the cell would be useful for researchers studying signal transduction, cell surface markers (such as integrins), and a variety of other applications.

Most pharmacological agents that act in steroid or steroid-like signaling pathways are agonists or antagonists of naturally occurring steroid-like molecule. These drugs often cause severe side effects both over the short and the long term. Many of these side effects could arise because the current drugs target both types of pathways, the classical transcriptional regulatory pathway and the rapid membrane pathway. By targeting only the rapid membrane aspect of the steroid action, and not the genomic portion (or vice-versa), it may be possible to generate novel therapeutic agents that will have fewer side effects.

II. The DPR-1 Receptor and the DPR-1 Receptor Family.

DPR-1 encodes a member of the nuclear hormone receptor (NHR) family as determined by sequence analysis (Table 1). The DNA binding domain of DPR-1 contains the signatures of NHR DNA binding domains, such as conserved spacing of two C4 zinc fingers, and conserved FF and GM dinucleotides. Similarity with other nuclear hormone receptors also extends into the ligand binding domain. DPR-1 defines a family of at least 21 nuclear hormone receptors in *C. elegans* that share homology throughout the DNA and ligand binding domains.

Among members of the NHR family, DPR-1 is most similar to the estrogen receptor-related family of proteins present in mammals including humans. Homology extends beyond the DNA binding domain to the ligand-binding domain, suggesting that DPR-1 may indeed bind a ligand. The ERRs may be the human equivalent of DPR-1.

To determine where and when DPR-1 is expressed, we performed in situ hybridization on mixed stage embryos (FIG. 1). Maternal transcripts were detected in early embryos, with higher concentrations in the embryonic germline, or P lineage. By the E8 stage (i.e., when there are 8 E, or endoderm, cells or ~100 total cells), zygotic transcripts can be detected in the developing endoderm cells. In later stages (bean and comma stages), DPR-1 transcripts are concentrated in the endoderm lineage, with some detectable transcripts in the pharynx. At the end of morphogenesis, the pretzel stage, transcripts are limited to the endoderm.

We examined the expression of zygotic DPR-1 using GFP::lacZ reporter fusions, and found that DPR-1 is expressed from the 4E cell stage (about 50 cells total in the early embryo) specifically in the endoderm lineage. This expression continues throughout the life of the worm (FIG. 1). Several cells in the head also express DPR-1. These cells may be the amphid neurons which, based on laser ablation experiments, normally prevent L1 stage larvae from entering the dauer state. It has been hypothesized that the dauer receptor might be located in these neurons.

Figure 3:
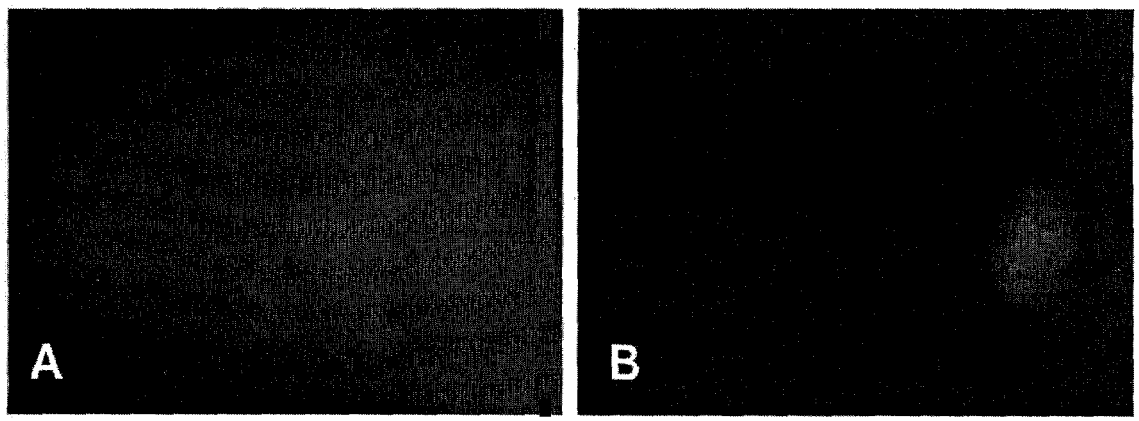
FIG. 3 shows that DPR-1 is present in the nucleus of early embryos. Panel A: DPR-1 (END-2) antibody staining of an approximately 16-cell embryo. DPR-1 is present in posterior nuclei of the embryo. Panel B shows detection of P granules using OICID4 antibody to mark the posterior of the embryo.
Figure 4:
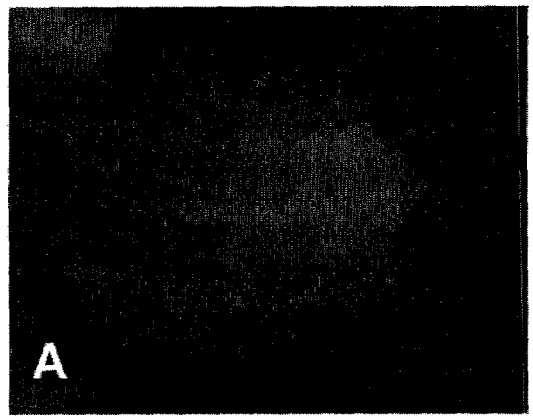
FIG. 4 shows that DPR-1 localizes to the membrane in later embryos. Panel A: E16 (16 E cells present, about 200 cells); Panel B: E20 (20 E cells present, about 300 cells); Panel C: comma stage embryos (about 300 cells) show DPR-1 staining around the perimeter of endodermal cells.
Figure 4:
Figure 4:
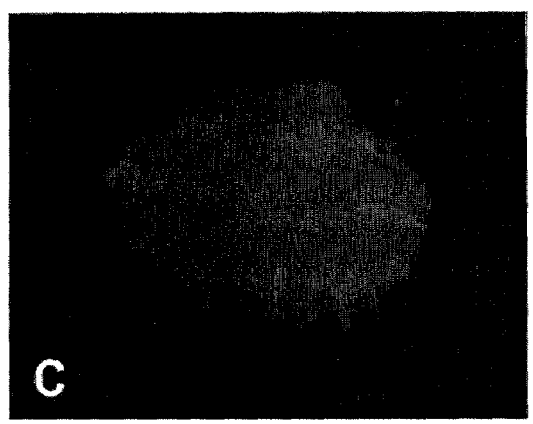

We generated antibodies to DPR-1 and examined the intracellular localization of DPR-1 protein in the developing embryo and larvae. In early embryos, DPR-1 is localized to posterior cells of the embryos and is in the nucleus, as expected for a nuclear hormone receptor (FIG. 3). However, by the E16 cell stage (about 200 total cells), the subcellular localization pattern of DPR-1 changes dramatically (FIG. 4). At this stage and beyond, DPR-1 no longer localizes the nucleus. Depending on the conditions under which mothers were cultured (see below), the staining is seen either throughout the cytoplasm and excluded from the nucleus, or almost exclusively at the margins (cortex) of the endoderm cells. At the E16 state, under conditions in which it is membrane-associated, DPR-1 is localized apically and along the lateral edges of the endoderm epithelial cells. By the comma (E20) stage, and throughout the rest of embryogenesis, DPR-1 is present throughout the cell cortex and is no longer excluded from the basal side.

Figure 6:
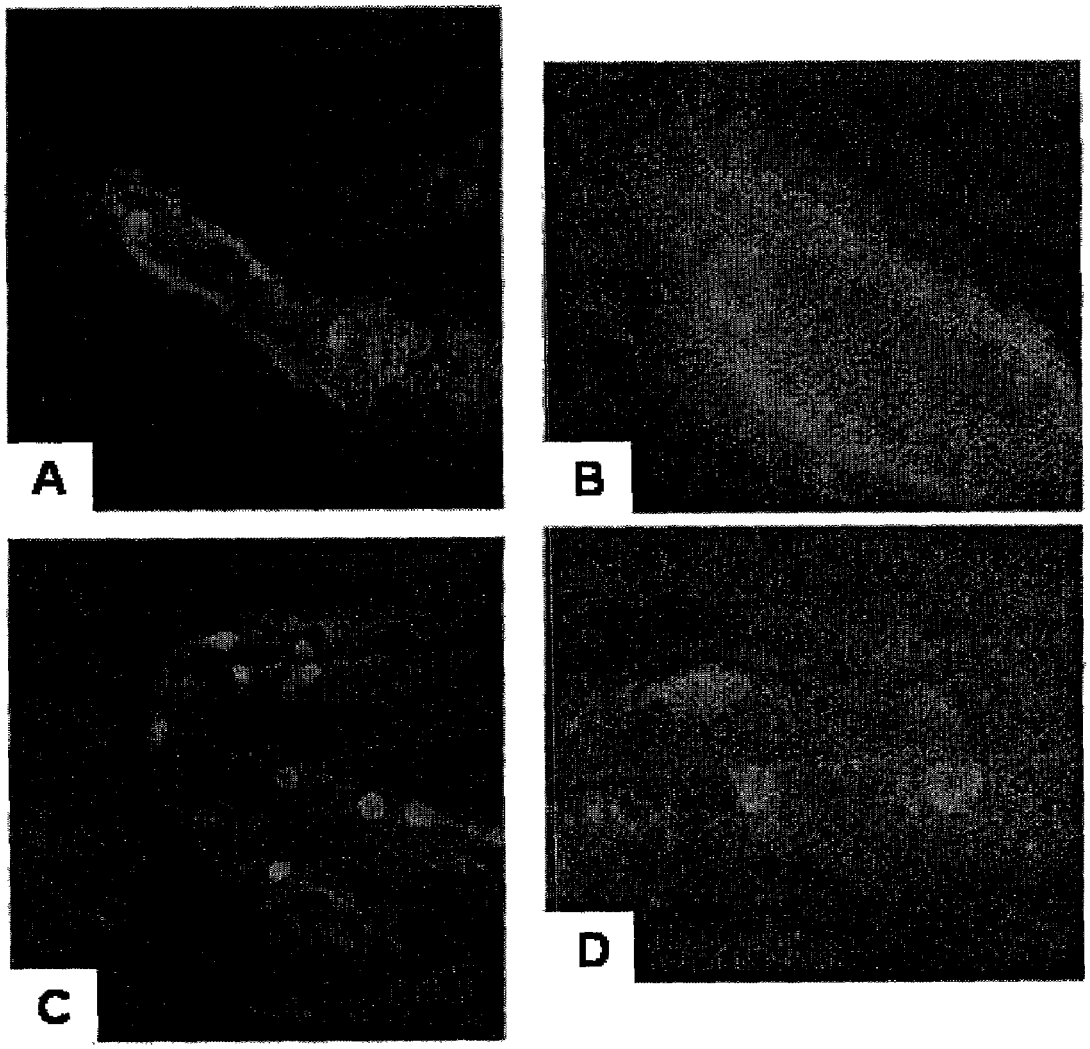
FIG. 6: Panel A shows DPR-1 staining at endoderm cell membranes. Panel B is a close up of panel A, showing nuclear exclusion of DPR-1. Panel C is an example of cytoplasmic staining of DPR-1. Panel D is a close up of panel C showing nuclear exclusion of DPR-1.
Figure 7:
FIG. 7 shows that DPR-1 is localized to the basal membrane in larvae. DPR-1 (END-2) outer labeling, MH33 inner labeling.

DPR-1 also displays two classes of staining pattern in larvae (as in embryos). Depending on the growth conditions, DPR-1 is either localized to the membrane or to the cytoplasm; again, it is specifically excluded from nuclei. When it is localized to the membrane of endoderm cells in larval stage worms, very little DPR-1 protein is detectable in the cytoplasm (compare with elt-2::GFP expression, FIG. 6). DPR-1 does not colocalize with the brush border antigen recognized by antibody MH33 (FIG. 7). Similar results are seen in L2 and L3 stage larvae (not shown).

Figure 2:
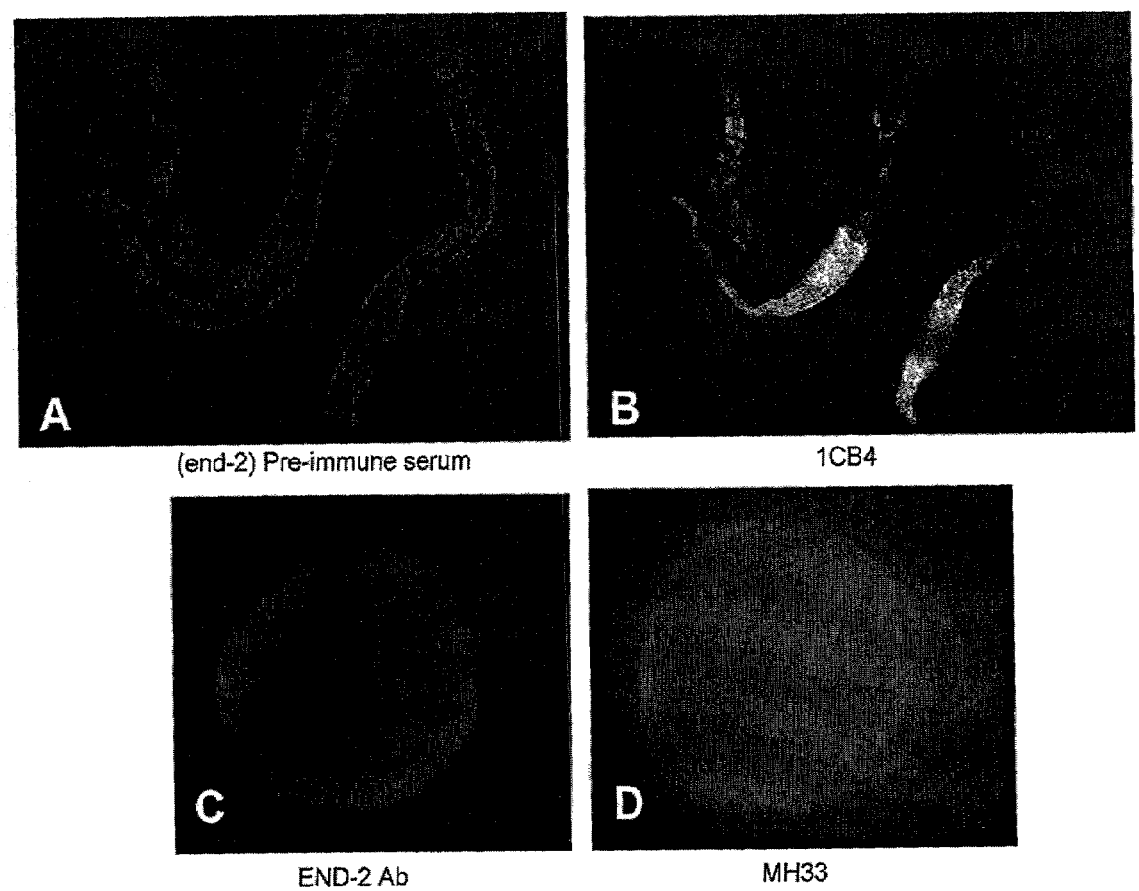
FIG. 2 demonstrates the specificity of DPR-1 antibody for DPR-1. Panel A: To test the specificity of the DPR-1 antibody, pre-immune serum was used in place of the DPR-1 antibody, and no staining was observed. Panel B: The larva were permeabilized, as shown by the staining of a control antibody, 1CB4, which, like DPR-1, stains endodermal cells. (Panel C, Panel D). DPR-1 was not detected in embryos carrying a deletion (itDf2) of the genomic region containing DPR-1. itDf2 embryos do not make endoderm. To confirm that the DPR-1 antibody does not detect an unrelated endoderm-specific antigen, we rescued endoderm development in itDf2 animals using end-1. These embryos contain endoderm, as revealed by the presence of gut-specific granules and the antigen detected by antibody MH33 (Panel D), yet DPR-1 is not detected (Panel C).

To confirm that our antibody recognizes DPR-1, we stained embryos that carry a chromosomal deletion of the endoderm determining region (EDR), a region on chromosome 5 in which DPR-1 resides. Such embryos normally do not generate endoderm at all; however, the lack of endoderm can be rescued by expression of any of three genes, end-1, -2, or -3, from a transgenic extrachromosomal array. END-1 and -3 are two GATA-type transcription factors that specify the endoderm. We found that embryos carrying a deletion of the EDR and an extrachromosomal end-1(+) gene do not stain with the DPR-1 antibody although they do produce endoderm (FIG. 2). This result suggests that the antibody recognizes DPR-1, which cannot be not made in the endoderm of these rescued embryos. Further, we found that embryos expressing DPR-1 ubiquitously from heat-shock-inducible expression vectors showed staining throughout all cells under conditions of induction (FIG. 6). In transgenic embryos expressing an DPR-1 reporter, the DPR-1 antibody stains nuclei of the same cells as those expressing a DPR-1::GFP fusion construct, indicating that the antibody is capable of recognizing DPR-1 protein. DPR-1 antibody recognizes a protein of the correct molecular weight on a western blot. Finally, competition experiments with the peptides used to produce the antibody also eliminated any signal, and pre-immune serum showed no staining. Collectively, these results suggest that the staining seen with DPR-1 antibody represents the genuine localization of the protein.

Figure 8:
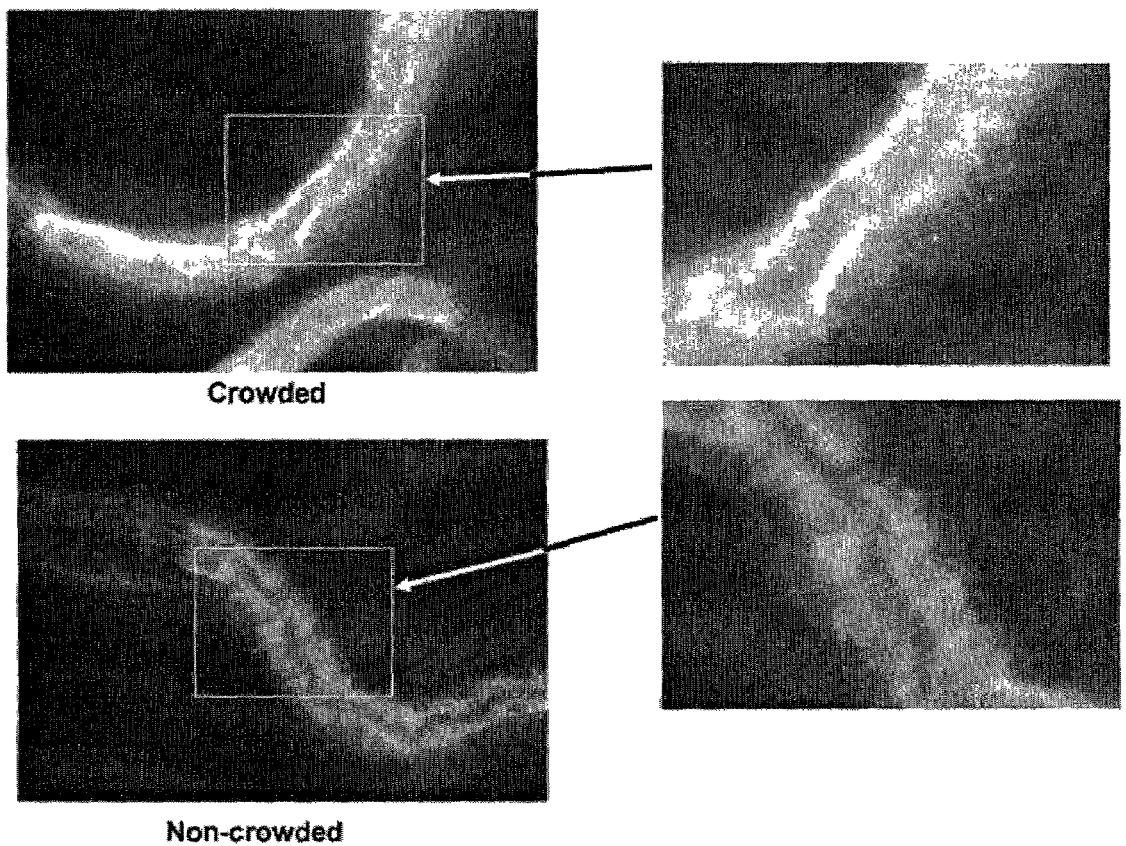
FIG. 8 shows that DPR-1 moves from the cytoplasm to the membrane when worms are crowded.

The two distinct staining patterns seen in both late embryos and larvae (i.e., cytoplasmic vs. membrane-associated) is attributable to the density at which worms are grown. Embryos derived from mothers grown at low density show primarily cytoplasmic staining; in embryos obtained from mothers grown under crowded conditions, it instead localizes to the membrane cortex (FIG. 8). The density at which larvae are cultured similarly determines where DPR-1 becomes localized: it is membrane-associated only in larvae grown at high density.

The extent of crowding in *C. elegans* is monitored by reception of dauer pheromone, an apparent mixture of lipid-like molecules that are continuously secreted by the worms. Dauer pheromone induces an alternative developmental state, the dauer larva, a long-lived desiccation-resistant larval form. This pheromone, obtained from medium in which *C. elegans* have been culture, has not been completely purified and its structure has not been precisely determined; however, it appears to be comprised of multiple compounds with chemical properties of hydroxylated fatty acids and bile acids. Such behavior is consistent with the possibility that dauer pheromone is a mixture of steroid-like molecules.

Figure 9:
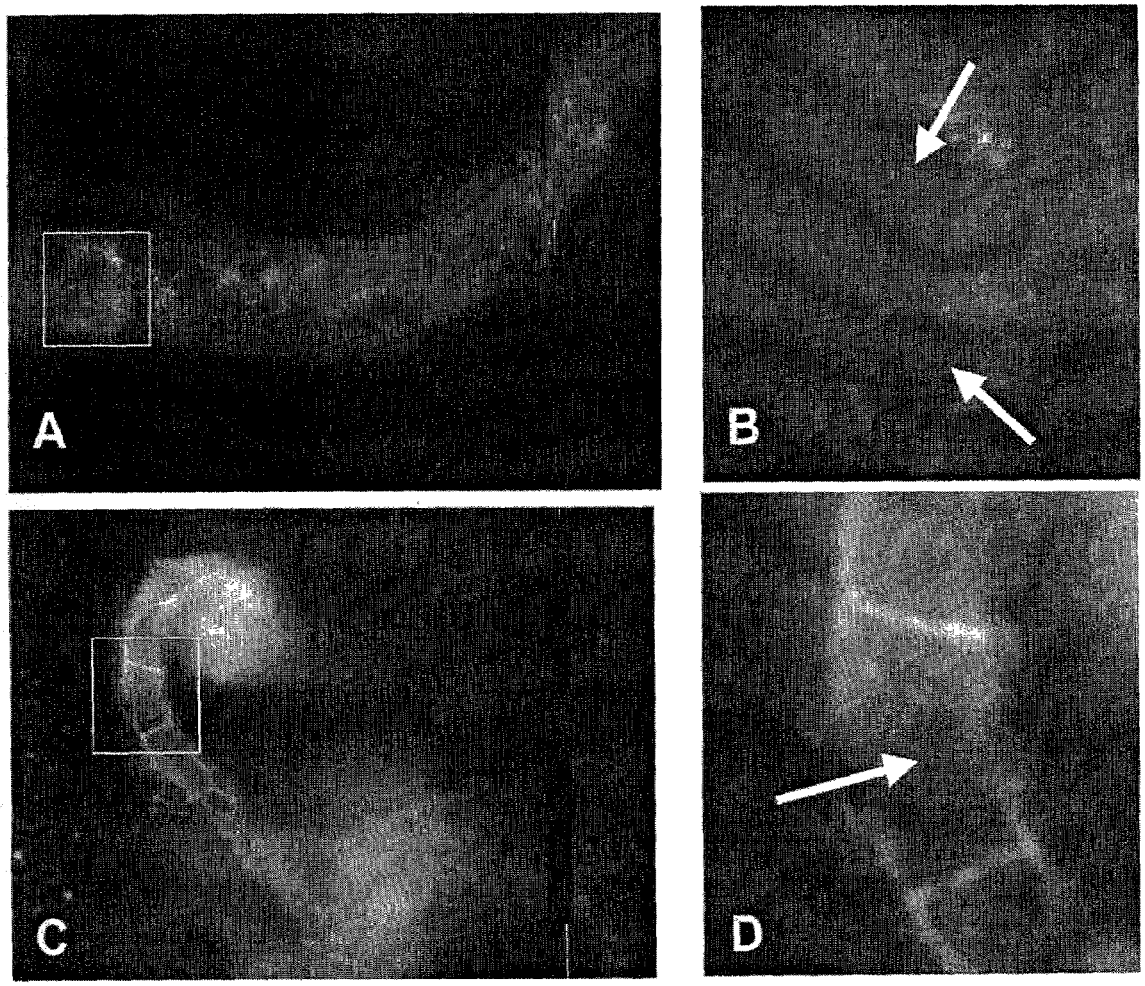
FIGS. 9A through 9D show that DPR-1 moves to the membrane in response to dauer pheromone.

Without being bound to a particular theory, we believe dauer pheromone is responsible for the relocalization of DPR-1 to the membrane under crowded conditions. Indeed, we found that sparsely cultured larvae treated with dauer pheromone causes DPR-1 to relocalize to the membrane, whereas untreated larvae continue to show cytoplasmic localization (FIG. 9). In larvae treated with dauer pheromone DPR-1 appeared to be more broadly associated with the membrane: instead of association exclusively with the basal membrane, it covered the entire perimeter of the cell. The response of DPR-1 to dauer pheromone appears to be graded (FIG. 10); at the highest levels of pheromone, a new pattern was observed in which the staining appeared more punctate and staining at the lateral margins between gut cells was not visible. Thus localization of DPR-1 within the cell is controlled by dauer pheromone and shows a graded response to this substance. The effect of the pheromone appears to be transmitted from mothers into their offspring, since the state of crowding of mothers apparently affects the intracellular localization of DPR-1 in late embryos.

Expression of the DPR-1 gene is influenced by the dauer state, further implicating it in the dauer pathway. Specifically, an DPR-1 gene reporter construct is repressed to undetectable levels in dauers, the only post-embryonic stage in which expression has not been observed. The down-regulation of DPR-1 expression may reflect a desensitization mechanism, which would be particularly appropriate if DPR-1 were the dauer receptor.

The pattern of DPR-1 is novel for a nuclear hormone receptor, leading us to address what function nuclear-excluded and membrane-associated DPR-1 might perform. We inhibited DPR-1 activity by performing RNA-mediated interference (RNAi) on L1 larva. A portion of L1 larva (91/766; 12%) treated with DPR-1 dsRNA grew slower than their siblings or L1s treated with a control dsRNA. While the majority of worms reached adulthood ~2.75 days after hatching, 11.6% of the DPR-1 (RNAi) worms were only at the L1, L2 or L3 stage at the same time (compared to 4.7% of worms soaked in control dsRNA). The effect of DPR-1 RNAi is more apparent at later times in which worms younger than adults were present 3.75, 4.75 and 5.75 days after hatching. In fact, some of the DPR-1(RNAi) worms (0.8%) were still at the L1 stage 5.75 days after hatching.

Only a portion of the DPR-1 (RNAi) larvae were affected. This may be due to incomplete inactivation of DPR-1 mRNA in some of the worms, such that DPR-1 is still expressed. Alternatively, other activities may be capable of compensating for the lack of DPR-1 in most cases. The delayed development if DPR-1 (RNAi) worms is temporary in that most worms do eventually develop to adulthood. It is possible that worms recover from the effects of RNAi and DPR-1 is expressed later in these animals, allowing growth to proceed. If DPR-1 is the receptor for dauer pheromone, removal of its function might lead to a dauer-defective phenotype; this possibility has not yet been tested.

While DPR-1 is localized to the nucleus in early embryos, as expected for a nuclear hormone receptor, its later localization to the cell membrane is novel, though not entirely unexpected. Evidence for the action of steroids in cell-surface signaling events has been accumulating. For example, 3% of the expressed estrogen receptor is detected at the cell surface in COS cells transfected with the gene encoding ERa and ERb. Addition of estrogen induces a rapid increase in IP3 production and adenylate cyclase activity. Non-internalizable ligands for NHRs have been shown to have effects for several different receptors in different cell types. The type of effect range from increased NO production, increased IP3 production, activation of JNK, and activation of adenylate cyclase. Some steroids have been shown to elicit effects independent of transcription.

DPR-1 may function as a typical NHR in early embryos, when it is located in the nucleus. However, in later embryos and larva, when the protein is located at the cell surface, it may function as a receptor linked to a second messenger system, as other artificially membrane bound NURs have been shown to do. Together these results indicate that DPR-1 and its relatives may provide a novel system for analyzing the mechanisms through which steroid-like molecules can act at the cell surface and for developing new pharmaceutical agents that interfere with this function.

The response of DPR-1, a steroid receptor-like protein, to dauer pheromone, an apparent mixture of molecules whose chemical behavior is consistent with a steroid-like structure, suggests that DPR-1 is a receptor for dauer pheromone. It is likely that that these other DPR-1 family members are also receptors for this pheromone. Distinct steroid-like molecules in the dauer pheromone mixture could bind to different DPR-1 family receptors. In this case, the large number of DPR-1 family members might result from the complexity of individual components in dauer pheromone. Different nematode species may express DPR-1 family members with different ligand specificities, thereby preventing cross-talk between dauer pheromone pathways of unrelated nematode species. Such a possibility is consistent with the observations that dauer pheromone shows species-specificity.

III. DPR-1 Family Members as Targets in Screening Systems.

In certain embodiments, this invention makes it possible to identify new pharmaceuticals and biological control agents that act on steroid-like signaling pathways. In addition this invention makes it possible to identify components in steroid-like signaling pathways, that can lead to generation of new steroid-like drugs, agricultural agents, and new kits for biotechnology.

IV. Assays for Modulators of DPR-1 Expression and/or Activity.

As indicated above, in one aspect, this invention is premised, in part, on the discovery of new class of nuclear hormone receptors that can be found in the cell membrane under certain conditions (DPR-1 receptors). These receptors are believed to be involved in a wide variety of physiological processes including, but not limited to the determination of various developmental pathways (e.g. cyst formation in nematodes)

In certain embodiments, modulators of these receptors (e.g. up- or down-regulation of receptor expression, inhibition or agonism of receptor activity, blocking of the receptor, etc.) will alter the metabolic activity of a cell. Thus, for example inhibitors of DPR-1 are expected to alter (e.g. inhibit or reverse) cyst formation in nematodes. Conversely, agonists are expected to induce cyst formation. Such agents are useful as pesticides or components of pesticides and/or in the development of biocontrol agents, particular for pathogenic nematodes.

Thus, in one embodiment, this invention provides methods of screening for agents that modulate expression and/or activity or DPR-1 or DPR-1 family receptors. In certain embodiments, the methods involve an DPR-1 or DPR-1 family receptor in a cell with a test agent; and detecting the metabolic activity of the cell wherein a difference in the metabolic activity of said cell as compared to the metabolic activity of a control cell indicates that said test agent is alters development of a nematode. Detection of changes in metabolic activity can involve detecting the expression level and/or activity level of DPR-1 family genes or gene products or the expression levels of other genes or gene products in the presence of the agent(s) in question.

Expression levels of a gene can be altered by changes in the transcription of the gene product (i.e. transcription of mRNA), and/or by changes in translation of the gene product (i.e. translation of the protein), and/or by post-translational modification(s) (e.g. protein folding, glycosylation, etc.). Thus preferred assays of this invention include assaying for level of transcribed mRNA (or other nucleic acids derived from the subject genes), level of translated protein, activity of translated protein, etc. Examples of such approaches are described below.

A) Nucleic-acid Based Assays.
  1) Target Molecules.

Changes in expression level can be detected by measuring changes in genomic DNA or a nucleic acid derived from the genomic DNA. In order to measure the expression level it is desirable to provide a nucleic acid sample for such analysis. In preferred embodiments the nucleic acid is found in or derived from a biological sample. The term "biological sample", as used herein, refers to a sample obtained from an organism or from components (e.g., cells) of an organism.

The sample may be of any biological tissue or fluid. Biological samples may also include organs or sections of tissues such as frozen sections taken for histological purposes.

The nucleic acid (e.g., mRNA or a nucleic acid derived from an mRNA) is, in certain preferred embodiments, isolated from the sample according to any of a number of methods well known to those of skill in the art. Methods of isolating mRNA are well known to those of skill in the art. For example, methods of isolation and purification of nucleic acids are described in detail in by Tijssen ed., (1993) Chapter 3 of *Laboratory Techniques in Biochemistry and Molecular Biology: Hybridization With Nucleic Acid Probes, Part I. Theory and Nucleic Acid Preparation*, Elsevier, N.Y. and Tijssen ed.

In a preferred embodiment, the "total" nucleic acid is isolated from a given sample using, for example, an acid guanidinium-phenol-chloroform extraction method and polyA+ mRNA is isolated by oligo dT column chromatography or by using (dT)n magnetic beads (see, e.g., Sambrook et al., *Molecular Cloning: A Laboratory Manual* (2nd ed.), Vols. 1–3, Cold Spring Harbor Laboratory, (1989), or *Current Protocols in Molecular Biology*, F. Ausubel et al., ed. (1987) Greene Publishing and Wiley-Interscience, New York).

Frequently, it is desirable to amplify the nucleic acid sample prior to assaying for expression level. Methods of amplifying nucleic acids are well known to those of skill in the art and include, but are not limited to polymerase chain reaction (PCR, see. e.g, Innis, et al., (1990) *PCR Protocols. A guide to Methods and Application*. Academic Press, Inc. San Diego,), ligase chain reaction (LCR) (see Wu and Wallace (1989) *Genomics* 4: 560, Landegren et al. (1988) *Science* 241: 1077, and Barringer et al. (1990) *Gene* 89: 117, transcription amplification (Kwoh et al. (1989) *Proc. Natl. Acad. Sci. USA* 86: 1173), self-sustained sequence replication (Guatelli et al. (1990) *Proc. Nat. Acad. Sci. USA* 87: 1874), dot PCR, and linker adapter PCR, etc.).

In a particularly preferred embodiment, where it is desired to quantify the transcription level (and thereby expression) (e.g. of an DPR-1 receptor or a gene under control of an DPR-1 receptor) in a sample, the nucleic acid sample is one in which the concentration of the mRNA transcript(s), or the concentration of the nucleic acids derived from the mRNA transcript(s), is proportional to the transcription level (and therefore expression level) of that gene. Similarly, it is preferred that the hybridization signal intensity be proportional to the amount of hybridized nucleic acid. While it is preferred that the proportionality be relatively strict (e.g., a doubling in transcription rate results in a doubling in mRNA transcript in the sample nucleic acid pool and a doubling in hybridization signal), one of skill will appreciate that the proportionality can be more relaxed and even non-linear. Thus, for example, an assay where a 5 fold difference in concentration of the target mRNA results in a 3 to 6 fold difference in hybridization intensity is sufficient for most purposes.

Where more precise quantification is required appropriate controls can be run to correct for variations introduced in sample preparation and hybridization as described herein. In addition, serial dilutions of "standard" target nucleic acids (e.g., mRNAs) can be used to prepare calibration curves according to methods well known to those of skill in the art. Of course, where simple detection of the presence or absence of a transcript or large differences of changes in nucleic acid concentration is desired, no elaborate control or calibration is require.

In the simplest embodiment, the sample nucleic acid sample is the total mRNA or a total cDNA isolated and/or otherwise derived from a biological sample. The nucleic acid may be isolated from the sample according to any of a number of methods well known to those of skill in the art as indicated above.

2) Hybridization-based Assays.

The expression of particular genes (e.g. genes encoding the DPR-1 receptor(s)) can be routinely accomplished using nucleic acid hybridization techniques (see, e.g., Sambrook et al. supra). For example, one method for evaluating the presence, absence, or quantity of a particular genomic DNA or reverse-transcribed cDNA involves a "Southern Blot". In a Southern Blot, the DNA typically fragmented and separated on an electrophoretic gel, is hybridized to a probe specific for the nucleic acid(s) of interest. Comparison of the intensity of the hybridization signal from the probe with a "control" probe (e.g. a probe for a "housekeeping gene) provides an estimate of the relative expression level of the target nucleic acid.

Alternatively, the mRNA can be directly quantified in a Northern blot. In brief, the mRNA is isolated from a given cell sample using, for example, an acid guanidinium-phenol-chloroform extraction method. The mRNA is then electrophoresed to separate the mRNA species and the mRNA is transferred from the gel to a nitrocellulose membrane. As with the Southern blots, labeled probes are used to identify and/or quantify the target mRNA. Appropriate controls (e.g. probes to housekeeping genes) provide a reference for evaluating relative expression level.

An alternative means for determining the particular nucleic acid expression levels is in situ hybridization. In situ hybridization assays are well known (e.g., Angerer (1987) *Meth. Enzymol* 152: 649). Generally, in situ hybridization comprises the following major steps: (1) fixation of tissue or biological structure to be analyzed; (2) prehybridization treatment of the biological structure to increase accessibility of target DNA, and to reduce nonspecific binding; (3) hybridization of the mixture of nucleic acids to the nucleic acid in the biological structure or tissue; (4) post-hybridization washes to remove nucleic acid fragments not bound in the hybridization and (5) detection of the hybridized nucleic acid fragments. The reagent used in each of these steps and the conditions for use vary depending on the particular application.

In some applications it is necessary to block the hybridization capacity of repetitive sequences. Thus, in some embodiments, tRNA, human genomic DNA, or Cot-1 DNA is used to block non-specific hybridization.

In certain embodiments, the gene(s) whose expression is altered by DPR-1 receptor modulation are unknown. Expression of such unknown genes can be determined in in array-based hybridization formats. Arrays are a multiplicity of different "probe" or "target" nucleic acids (or other compounds) attached to one or more surfaces (e.g., solid, membrane, or gel). In a preferred embodiment, the multiplicity of nucleic acids (or other moieties) is attached to a single contiguous surface or to a multiplicity of surfaces juxtaposed to each other.

In an array format a large number of different hybridization reactions can be run essentially "in parallel." This provides rapid, essentially simultaneous, evaluation of a number of hybridizations in a single "experiment". Methods of performing hybridization reactions in array based formats are well known to those of skill in the art (see, e.g., Pastinen (1997) *Genome Res.* 7: 606–614; Jackson (1996) *Nature*

*Biotechnology* 14:1685; Chee (1995) *Science* 274: 610; WO 96/17958, Pinkel et al. (1998) *Nature Genetics* 20: 207–211).

Arrays, particularly nucleic acid arrays can be produced according to a wide variety of methods well known to those of skill in the art. For example, in a simple embodiment, "low density" arrays can simply be produced by spotting (e.g. by hand using a pipette) different nucleic acids at different locations on a solid support (e.g. a glass surface, a membrane, etc.).

This simple spotting, approach has been automated to produce high density spotted arrays (see, e.g., U.S. Pat. No: 5,807,522). This patent describes the use of an automated system that taps a microcapillary against a surface to deposit a small volume of a biological sample. The process is repeated to generate high density arrays.

Arrays can also be produced using oligonucleotide synthesis technology. Thus, for example, U.S. Pat. No. 5,143,854 and PCT Patent Publication Nos. WO 90/15070 and 92/10092 teach the use of light-directed combinatorial synthesis of high density oligonucleotide arrays. Synthesis of high density arrays is also described in U.S. Pat. Nos. 5,744,305, 5,800,992 and 5,445,934.

3) Amplification-based Assays.

In another embodiment, amplification-based assays can be used to measure expression (transcription) level of particular genes (e.g. genes identified from the array hybridization discussed above). In such amplification-based assays, the target nucleic acid sequences act as template(s) in amplification reaction(s) (e.g. Polymerase Chain Reaction (PCR) or reverse-transcription PCR (RT-PCR)). In a quantitative amplification, the amount of amplification product will be proportional to the amount of template in the original sample. Comparison to appropriate (e.g. healthy tissue or cells unexposed to the test agent) controls provides a measure of the target transcript level.

Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. Detailed protocols for quantitative PCR are provided in Innis et al. (1990) *PCR Protocols, A Guide to Methods and Applications*, Academic Press, Inc. N.Y.). One approach, for example, involves simultaneously co-amplifying a known quantity of a control sequence using the same primers as those used to amplify the target. This provides an internal standard that may be used to calibrate the PCR reaction.

4) Optimization of Assay Formats.

As indicated above a variety of nucleic acid hybridization formats are known to those skilled in the art. For example, common formats include sandwich assays and competition or displacement assays. Such assay formats are generally described in Hames and Higgins (1985) *Nucleic Acid Hybridization, A Practical Approach*, IRL Press; Gall and Pardue (1969) *Proc. Natl. Acad. Sci. USA* 63: 378–383; and John et al. (1969) *Nature* 223: 582–587.

Sandwich assays are commercially useful hybridization assays for detecting or isolating nucleic acid sequences. Such assays utilize a "capture" nucleic acid covalently immobilized to a solid support and a labeled "signal" nucleic acid in solution. The sample will provide the target nucleic acid. The "capture" nucleic acid and "signal" nucleic acid probe hybridize with the target nucleic acid to form a "sandwich" hybridization complex. To be most effective, the signal nucleic acid should not hybridize with the capture nucleic acid.

Typically, labeled signal nucleic acids are used to detect hybridization. Complementary nucleic acids or signal nucleic acids may be labeled by any one of several methods typically used to detect the presence of hybridized polynucleotides. The most common method of detection is the use of autoradiography with $^3$H, $^{125}$I, $^{35}$S, $^{14}$C, or $^{32}$P-labeled probes or the like. Other labels include ligands that bind to labeled antibodies, fluorophores, chemi-luminescent agents, enzymes, and antibodies which can serve as specific binding pair members for a labeled ligand.

Detection of a hybridization complex may require the binding of a signal generating complex to a duplex of target and probe polynucleotides or nucleic acids. Typically, such binding occurs through ligand and anti-ligand interactions as between a ligand-conjugated probe and an anti-ligand conjugated with a signal.

The sensitivity of the hybridization assays may be enhanced through use of a nucleic acid amplification system that multiplies the target nucleic acid being detected. Examples of such systems include the polymerase chain reaction (PCR) system and the ligase chain reaction (LCR) system. Other methods recently described in the art are the nucleic acid sequence based amplification (NASBAO, Cangene, Mississauga, Ontario) and Q Beta Replicase systems.

Nucleic acid hybridization simply involves providing a denatured probe(s) and target nucleic acid(s) under conditions where the probe and its complementary target can form stable hybrid duplexes through complementary base pairing. The nucleic acids that do not form hybrid duplexes are then washed away leaving the hybridized nucleic acids to be detected, typically through detection of an attached detectable label. It is generally recognized that nucleic acids are denatured by increasing the temperature or decreasing the salt concentration of the buffer containing the nucleic acids, or in the addition of chemical agents, or the raising of the pH. Under low stringency conditions (e.g., low temperature and/or high salt and/or high target concentration) hybrid duplexes (e.g., DNA:DNA, RNA:RNA, or RNA:DNA) will form even where the annealed sequences are not perfectly complementary. Thus specificity of hybridization is reduced at lower stringency. Conversely, at higher stringency (e.g., higher temperature or lower salt) successful hybridization requires fewer mismatches.

One of skill in the art will appreciate that hybridization conditions may be selected to provide any degree of stringency. In a preferred embodiment, hybridization is performed at low stringency to ensure hybridization and then subsequent washes are performed at higher stringency to eliminate mismatched hybrid duplexes. Successive washes may be performed at increasingly higher stringency (e.g., down to as low as 0.25×SSPE at 37° C. to 70° C.) until a desired level of hybridization specificity is obtained. Stringency can also be increased by addition of agents such as formamide. Hybridization specificity may be evaluated by comparison of hybridization to the test probes with hybridization to the various controls that can be present.

In general, there is a tradeoff between hybridization specificity (stringency) and signal intensity. Thus, in a preferred embodiment, the wash is performed at the highest stringency that produces consistent results and that provides a signal intensity greater than approximately 10% of the background intensity. Thus, in a preferred embodiment, the hybridized array may be washed at successively higher stringency solutions and read between each wash. Analysis of the data sets thus produced will reveal a wash stringency above which the hybridization pattern is not appreciably altered and which provides adequate signal for the particular probes of interest.

In a preferred embodiment, background signal is reduced by the use of a blocking reagent (e.g., tRNA, sperm DNA, cot-1 DNA, etc.) during the hybridization to reduce non-specific binding. The use of blocking agents in hybridization is well known to those of skill in the art (see, e.g., Chapter 8 in P. Tijssen, supra.)

Methods of optimizing hybridization conditions are well known to those of skill in the art (see, e.g., Tijssen (1993) *Laboratory Techniques in Biochemistry and Molecular Biology, Vol. 24: Hybridization With Nucleic Acid Probes*, Elsevier, N.Y.).

Optimal conditions are also a function of the sensitivity of label (e.g., fluorescence) detection for different combinations of substrate type, fluorochrome, excitation and emission bands, spot size and the like. Low fluorescence background surfaces can be used (see, e.g., Chu (1992) *Electrophoresis* 13:105–114). The sensitivity for detection of spots ("target elements") of various diameters on the candidate surfaces can be readily determined by, e.g., spotting a dilution series of fluorescently end labeled DNA fragments. These spots are then imaged using conventional fluorescence microscopy. The sensitivity, linearity, and dynamic range achievable from the various combinations of fluorochrome and solid surfaces (e.g., glass, fused silica, etc.) can thus be determined. Serial dilutions of pairs of fluorochrome in known relative proportions can also be analyzed. This determines the accuracy with which fluorescence ratio measurements reflect actual fluorochrome ratios over the dynamic range permitted by the detectors and fluorescence of the substrate upon which the probe has been fixed.

Probes used in the methods of this invention can be full length (the length of the target nucleic acid) or less than full length. Shorter probes are empirically tested for specificity. Preferred probes are sufficiently long so as to specifically hybridize with the target nucleic acid(s) under stringent conditions. The preferred size range is from about 20 bases to the length of the target nucleic acid, more preferably from about 30 bases to the length of the target nucleic acid, and most preferably from about 40 bases to the length of the target nucleic acid.

The probes are typically labeled, with a detectable label. Detectable labels suitable for use in the present invention include any composition detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent dyes (e.g., fluorescein, texas red, rhodamine, green fluorescent protein, and the like, see, e.g., Molecular Probes, Eugene, Oregon, USA), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold (e.g., gold particles in the 40–80 nm diameter size range scatter green light with high efficiency) or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

Desirably, fluorescent labels should absorb light above about 300 nm, preferably about 350 nm, and more preferably above about 400 nm, usually emitting at wavelengths greater than about 10 nm higher than the wavelength of the light absorbed. It should be noted that the absorption and emission characteristics of the bound dye can differ from the unbound dye. Therefore, when referring to the various wavelength ranges and characteristics of the dyes, it is intended to indicate the dyes as employed and not the dye which is unconjugated and characterized in an arbitrary solvent.

The label may be added to the target (sample) nucleic acid(s) prior to, or after the hybridization. So called "direct labels" are detectable labels that are directly attached to or incorporated into the target (sample) nucleic acid prior to hybridization. In contrast, so called "indirect labels" are joined to the hybrid duplex after hybridization. Often, the indirect label is attached to a binding moiety that has been attached to the target nucleic acid prior to the hybridization. Thus, for example, the target nucleic acid may be biotinylated before the hybridization. After hybridization, an avidin-conjugated fluorophore will bind the biotin bearing hybrid duplexes providing a label that is easily detected. For a detailed review of methods of labeling nucleic acids and detecting labeled hybridized nucleic acids see *Laboratory Techniques in Biochemistry and Molecular Biology, Vol. 24: Hybridization With Nucleic Acid Probes*, P. Tijssen, ed. Elsevier, N.Y., (1993)).

Fluorescent labels are easily added during an in vitro transcription reaction. Thus, for example, fluorescein labeled UTP and CTP can be incorporated into the RNA produced in an in vitro transcription.

The labels can be attached directly or through a linker moiety. In general, the site of label or linker-label attachment is not limited to any specific position. For example, a label may be attached to a nucleoside, nucleotide, or analogue thereof at any position that does not interfere with detection or hybridization as desired. For example, certain Label-On Reagents from Clontech (Palo Alto, Calif.) provide for labeling interspersed throughout the phosphate backbone of an oligonucleotide and for terminal labeling at the 3' and 5' ends. As shown for example herein, labels can be attached at positions on the ribose ring or the ribose can be modified and even eliminated as desired. The base moieties of useful labeling reagents can include those that are naturally occurring or modified in a manner that does not interfere with the purpose to which they are put. Modified bases include but are not limited to 7-deaza A and G, 7-deaza-8-aza A and G, and other heterocyclic moieties.

It will be recognized that fluorescent labels are not to be limited to single species organic molecules, but include inorganic molecules, multi-molecular mixtures of organic and/or inorganic molecules, crystals, heteropolymers, and the like. Thus, for example, CdSe-CdS core-shell nanocrystals enclosed in a silica shell can be easily derivatized for coupling to a biological molecule (Bruchez et al. (1998) *Science*, 281: 2013–2016). Similarly, highly fluorescent quantum dots (zinc sulfide-capped cadmium selenide) have been covalently coupled to biomolecules for use in ultrasensitive biological detection (Warren and Nie (1998) *Science*, 281: 2016–2018).

B) Polypeptide-based Assays—Polypeptide Expression.

1) Assay Formats.

In addition to, or in alternative to, the detection of nucleic acid expression level(s), alterations in expression of DPR-1 family receptors can be detected and/or quantified by detecting and/or quantifying the amount and/or activity of translated DPR-1 polypeptide or fragments thereof. Similarly the detection of other polypeptides whose expression is ultimately modulated by DPR-1 (e.g. as identified in an array hybridization) can be assayed by detecting and/or quantifying the amount and/or activity of translated polypeptide or fragments thereof.

2) Detection of Expressed Protein.

The polypeptides to be asssayed can be detected and quantified by any of a number of methods well known to those of skill in the art. These may include analytic biochemical methods such as electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), immunoelectrophoresis, radioimmunoassay (RIA), enzyme-linked immunosorbent assays (ELISAs), immunofluorescent assays, western blotting, and the like.

In one preferred embodiment, the polypeptide(s) are detected/quantified in an electrophoretic protein separation (e.g. a 1- or 2-dimensional electrophoresis). Means of detecting proteins using electrophoretic techniques are well known to those of skill in the art (see generally, R. Scopes (1982) *Protein Purification*, Springer-Verlag, N.Y.; Deutscher, (1990) *Methods in Enzymology Vol. 182: Guide to Protein Purification*, Academic Press, Inc., N.Y.).

In another preferred embodiment, Western blot (immunoblot) analysis is used to detect and quantify the presence of polypeptide(s) of this invention in the sample. This technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind the target polypeptide(s).

The antibodies specifically bind to the target polypeptide(s) and may be directly labeled or alternatively may be subsequently detected using labeled antibodies (e.g., labeled sheep anti-mouse antibodies) that specifically bind to the a domain of the antibody.

In preferred embodiments, the polypeptide(s) (e.g. DPR-1 recptors) are detected using an immunoassay. As used herein, an immunoassay is an assay that utilizes an antibody to specifically bind to the analyte (e.g., the target polypeptide(s)). The immunoassay is thus characterized by detection of specific binding of a polypeptide of this invention to an antibody as opposed to the use of other physical or chemical properties to isolate, target, and quantify the analyte.

Any of a number of well recognized immunological binding assays (see, e.g., U.S. Pat. Nos. 4,366,241; 4,376, 110; 4,517,288; and 4,837,168) are well suited to detection or quantification of the polypeptide(s) identified herein. For a review of the general immunoassays, see also Asai (1993) *Methods in Cell Biology Volume 37: Antibodies in Cell Biology*, Academic Press, Inc. New York; Stites & Terr (1991) *Basic and Clinical Immunology 7th Edition.*

Immunological binding assays (or immunoassays) typically utilize a "capture agent" to specifically bind to and often immobilize the analyte. In preferred embodiments, the capture agent is an antibody.

Immunoassays also often utilize a labeling agent to specifically bind to and label the binding complex formed by the capture agent and the analyte. The labeling agent may itself be one of the moieties comprising the antibody/analyte complex. Thus, the labeling agent may be a labeled polypeptide or a labeled antibody that specifically recognizes the already bound target polypeptide. Alternatively, the labeling agent may be a third moiety, such as another antibody, that specifically binds to the capture agent/polypeptide complex.

Other proteins capable of specifically binding immunoglobulin constant regions, such as protein A or protein G may also be used as the label agent. These proteins are normal constituents of the cell walls of streptococcal bacteria. They exhibit a strong non-immunogenic reactivity with immunoglobulin constant regions from a variety of species (see, generally Kronval, et al. (1973) *J. Immunol.*, 111: 1401–1406, and Akerstrom (1985) *J. Immunol.*, 135: 2589–2542).

Preferred immunoassays for detecting the target polypeptide(s) are either competitive or noncompetitive. Noncompetitive immunoassays are assays in which the amount of captured analyte is directly measured. In one preferred "sandwich" assay, for example, the capture agents (antibodies) can be bound directly to a solid substrate where they are immobilized. These immobilized antibodies then capture the target polypeptide present in the test sample. The target polypeptide thus immobilized is then bound by a labeling agent, such as a second antibody bearing a label.

In competitive assays, the amount of analyte (e.g. DPR-1 receptor) present in the sample is measured indirectly by measuring the amount of an added (exogenous) analyte displaced (or competed away) from a capture agent (antibody) by the analyte present in the sample. For example, in one competitive assay, a known amount of, labeled DPR-1 receptor is added to the sample and the sample is then contacted with a capture agent. The amount of labeled polypeptide bound to the antibody is inversely proportional to the concentration of target polypeptide present in the sample.

In one particularly preferred embodiment, the antibody is immobilized on a solid substrate. The amount of target polypeptide bound to the antibody may be determined either by measuring the amount of target polypeptide present in a polypeptide/antibody complex, or alternatively by measuring the amount of remaining uncomplexed polypeptide.

The immunoassay methods of the present invention include an enzyme immunoassay (EIA) which utilizes, depending on the particular protocol employed, unlabeled or labeled (e.g., enzyme-labeled) derivatives of polyclonal or monoclonal antibodies or antibody fragments or single-chain antibodies. In certain embodiments the antibodies are antibodies that bind to an DPR-1 receptor. Any of the known modifications of EIA, for example, enzyme-linked immunoabsorbent assay (ELISA), may also be employed. As indicated above, also contemplated by the present invention are immunoblotting immunoassay techniques such as western blotting employing an enzymatic detection system.

The immunoassay methods of the present invention may also include other known immunoassay methods, for example, fluorescent immunoassays using antibody conjugates or antigen conjugates of fluorescent substances such as fluorescein or rhodamine, latex agglutination with antibody-coated or antigen-coated latex particles, haemagglutination with antibody-coated or antigen-coated red blood corpuscles, and immunoassays employing an avidin-biotin or strepavidin-biotin detection systems, and the like.

The particular parameters employed in the immunoassays of the present invention can vary widely depending on various factors such as the concentration of antigen in the sample, the nature of the sample, the type of immunoassay employed and the like. Optimal conditions can be readily established by those of ordinary skill in the art. In certain embodiments, the amount of antibody that binds DPR-1 polypeptide is typically selected to give 50% binding of detectable marker in the absence of sample. If purified antibody is used as the antibody source, the amount of antibody used per assay will generally range from about 1 ng to about 100 ng. Typical assay conditions include a temperature range of about 4° C. to about 45° C., preferably about 25° C. to about 37° C., and most preferably about 25° C., a pH value range of about 5 to 9, preferably about 7, and an ionic strength varying from that of distilled water to that of about 0.2M sodium chloride, preferably about that of 0.15M sodium chloride. Times will vary widely depending upon the nature of the assay, and generally range from about 0.1 minute to about 24 hours. A wide variety of buffers, for example PBS, may be employed, and other reagents such as salt to enhance ionic strength, proteins such as serum albumins, stabilizers, biocides and non-ionic detergents may also be included.

The assays of this invention are scored (as positive or negative or quantity of target polypeptide) according to standard methods well known to those of skill in the art. The particular method of scoring will depend on the assay format and choice of label. For example, a Western Blot assay can be scored by visualizing the colored product produced by the enzymatic label. A clearly visible colored band or spot at the correct molecular weight is scored as a positive result, while the absence of a clearly visible spot or band is scored as a negative. The intensity of the band or spot can provide a quantitative measure of target polypeptide concentration.

Antibodies for use in the various immunoassays described herein, are commercially available or can be produced as described below.

3) Antibodies to DPR-1 Receptors.

Either polyclonal or monoclonal antibodies (e.g., anti-DPR-1 receptor antibodies may be used in the immunoassays of the invention described herein. Polyclonal antibodies are preferably raised by multiple injections (e.g. subcutaneous or intramuscular injections) of substantially pure polypeptides (e.g. DPR-1 or fragments thereof) or antigenic polypeptides into a suitable non-human mammal. The antigenicity of the target peptides can be determined by conventional techniques to determine the magnitude of the antibody response of an animal that has been immunized with the peptide. Generally, the peptides that are used to raise antibodies for use in the methods of this invention should generally be those which induce production of high titers of antibody with relatively high affinity for target polypeptide.

If desired, the immunizing peptide may be coupled to a carrier protein by conjugation using techniques that are well-known in the art. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (e.g. a mouse or a rabbit).

The antibodies are then obtained from blood samples taken from the mammal. The techniques used to develop polyclonal antibodies are known in the art (see, e.g., *Methods of Enzymology*, "Production of Antisera With Small Doses of Immunogen: Multiple Intradermal Injections", Langone, et al. eds. (Acad. Press, 1981)). Polyclonal antibodies produced by the animals can be further purified, for example, by binding to and elution from a matrix to which the peptide to which the antibodies were raised is bound. Those of skill in the art will know of various techniques common in the immunology arts for purification and/or concentration of polyclonal antibodies, as well as monoclonal antibodies see, for example, Coligan, et al. (1991) Unit 9, *Current Protocols in Immunology*, Wiley Interscience).

Preferably, however, the antibodies produced will be monoclonal antibodies ("mAb's"). For preparation of monoclonal antibodies, immunization of a mouse or rat is preferred. The term "antibody" as used in this invention includes intact molecules as well as fragments thereof, such as, Fab and $F(ab')^{2'}$, and/or single-chain antibodies (e.g. scFv) which are capable of binding an epitopic determinant.

The general method used for production of hybridomas secreting mAbs is well known (Kohler and Milstein (1975) *Nature*, 256:495). Briefly, as described by Kohler and Milstein the technique comprises fusing an antibody-secreting cell (e.g. a splenocyte) with an immortalized cell (e.g. a myeloma cell). Hybridomas are then screened for production of antibodies that bind to DPR-1 or a fragment thereof. Confirmation of specificity among mAb's can be accomplished using relatively routine screening techniques (such as the enzyme-linked immunosorbent assay, or "ELISA", BiaCore, etc.) to determine the binding specificity and/or avidity of the mAb of interest.

Antibodies fragments, e.g. single chain antibodies (scFv or others), can also be produced/selected using phage display technology. The ability to express antibody fragments on the surface of viruses that infect bacteria (bacteriophage or phage) makes it possible to isolate a single binding antibody fragment, e.g., from a library of greater than $10^{10}$ nonbinding clones. To express antibody fragments on the surface of phage (phage display), an antibody fragment gene is inserted into the gene encoding a phage surface protein (e.g., pIII) and the antibody fragment-pIII fusion protein is displayed on the phage surface (McCafferty et al. (1990) *Nature*, 348: 552–554; Hoogenboom et al. (1991) *Nucleic Acids Res.* 19: 4133–4137).

Since the antibody fragments on the surface of the phage are functional, phage bearing antigen binding antibody fragments can be separated from non-binding phage by antigen affinity chromatography (McCafferty et al. (1990) *Nature*, 348: 552–554). Depending on the affinity of the antibody fragment, enrichment factors of 20 fold-1,000,000 fold are obtained for a single round of affinity selection. By infecting bacteria with the eluted phage, however, more phage can be grown and subjected to another round of selection. In this way, an enrichment of 1000 fold in one round can become 1,000,000 fold in two rounds of selection (McCafferty et al. (1990) *Nature*, 348: 552–554). Thus even when enrichments are low (Marks et al. (1991) *J. Mol. Biol.* 222: 581–597), multiple rounds of affinity selection can lead to the isolation of rare phage. Since selection of the phage antibody library on antigen results in enrichment, the majority of clones bind antigen after as few as three to four rounds of selection. Thus only a relatively small number of clones (several hundred) need to be analyzed for binding to antigen.

Human antibodies can be produced without prior immunization by displaying very large and diverse V-gene repertoires on phage (Marks et al. (1991) *J. Mol. Biol.* 222: 581–597). In one embodiment natural $V_H$ and $V_L$ repertoires present in human peripheral blood lymphocytes are were isolated from unimmunized donors by PCR. The V-gene repertoires were spliced together at random using PCR to create a scFv gene repertoire which is was cloned into a phage vector to create a library of 30 million phage antibodies (Id.). From this single "naive" phage antibody library, binding antibody fragments have been isolated against more than 17 different antigens, including haptens, polysaccharides and proteins (Marks et al. (1991) *J. Mol. Biol.* 222: 581–597; Marks et al. (1993). *Biol/Technology.* 10: 779–783; Griffiths et al. (1993) *EMBO J.* 12: 725–734; Clackson et al. (1991) *Nature*. 352: 624–628). Antibodies have been produced against self proteins, including human thyroglobulin, immunoglobulin, tumor necrosis factor and CEA (Griffiths et al. (1993) *EMBO J.* 12: 725–734). It is also possible to isolate antibodies against cell surface antigens by selecting directly on intact cells. The antibody fragments are highly specific for the antigen used for selection and have affinities in the 1:M to 100 nM range (Marks et al. (1991) *J. Mol. Biol.* 222: 581–597; Griffiths et al. (1993) *EMBO J.* 12: 725-734). Larger phage antibody libraries result in the isolation of more antibodies of higher binding affinity to a greater proportion of antigens.

It will also be recognized that antibodies can be prepared by any of a number of commercial services (e.g., Berkeley antibody laboratories, Bethyl Laboratories, Anawa, Eurogenetec, etc.).

C) Polypeptide-based Assays—Polypeptide Activity.

In addition to, or as an alternative to, the assays described above, it is also possible to assay for DPR-1 receptor activity. As explained above, the DPR-1 family are nuclear hormone receptors. Thus, endogenous DPR-1 activity in a cell can be readily measured by providing a suitable ligand (e.g. one identified according to the methods described herein) and detecting activity in response to the ligand (e.g. induction of gene transcription, induction of second messenger, etc.).

D) Pre-screening for Agents that Bind DPR-1 Nucleic Acids or Polypeptides.

In certain embodiments it is desired to pre-screen test agents for the ability to interact with (e.g. specifically bind to) an DPR-1 family nucleic acid or polypeptide. Specifically, binding test agents are more likely to interact with and thereby modulate DPR-1 receptor expression and/or activity. Thus, in some preferred embodiments, the test agent(s) are pre-screened for binding DPR-1 family nucleic acids or to DPR-1 family receptors before performing the more complex assays described above.

In one embodiment, such pre-screening is accomplished with simple binding assays. Means of assaying for specific binding or the binding affinity of a particular ligand for a nucleic acid or for a protein are well known to those of skill in the art. In preferred binding assays, the DPR-1 receptor protein or protein fragment, or nucleic acid is immobilized and exposed to a test agent (which can be labeled), or alternatively, the test agent(s) are immobilized and exposed to an DPR-1 family protein (or fragment) or to an DPR-1 family nucleic acid or fragment thereof (which can be labeled). The immobilized moiety is then washed to remove any unbound material and the bound test agent or bound DPR-1 nucleic acid or protein is detected (e.g. by detection of a label attached to the bound molecule). The amount of immobilized label is proportional to the degree of binding between the DPR-1 family protein or nucleic acid and the test agent.

V. High Throughput Screening for Agents that Modulate DPR-1 Expression and/or Activity.

The assays for modulators of DPR-1 expression and/or activity or DPR-1 ligands are also amenable to "high-throughput" modalities. Conventionally, new chemical entities with useful properties (e.g., modulation of DPR-1 activity and/or expression) are generated by identifying a chemical compound (called a "lead compound") with some desirable property or activity, creating variants of the lead compound, and evaluating the property and activity of those variant compounds. However, the current trend is to shorten the time scale for all aspects of drug discovery. Because of the ability to test large numbers quickly and efficiently, high throughput screening (HTS) methods are replacing conventional lead compound identification methods.

In one preferred embodiment, high throughput screening methods involve providing a library containing a large number of compounds (candidate compounds) potentially having the desired activity. Such "combinatorial chemical libraries" are then screened in one or more assays, as described herein, to identify those library members (particular chemical species or subclasses) that display a desired characteristic activity. The compounds thus identified can serve as conventional "lead compounds" or can themselves be used directly in the desired application.

A) Combinatorial Chemical Libraries for Modulators of DPR-1 Expression or Activity.

The likelihood of an assay identifying an that modulates DPR-1 receptor activity and/or expression is increased when the number and types of test agents used in the screening system is increased. Recently, attention has focused on the use of combinatorial chemical libraries to assist in the generation of new chemical compound leads. A combinatorial chemical library is a collection of diverse chemical compounds generated by either chemical synthesis or biological synthesis by combining a number of chemical "building blocks" such as reagents. For example, a linear combinatorial chemical library such as a polypeptide library is formed by combining a set of chemical building blocks called amino acids in every possible way for a given compound length (i.e., the number of amino acids in a polypeptide compound). Millions of chemical compounds can be synthesized through such combinatorial mixing of chemical building blocks. For example, one commentator has observed that the systematic, combinatorial mixing of 100 interchangeable chemical building blocks results in the theoretical synthesis of 100 million tetrameric compounds or 10 billion pentameric compounds (Gallop et al. (1994) 37(9): 1233–1250).

Preparation and screening of combinatorial chemical libraries is well known to those of skill in the art. Such combinatorial chemical libraries include, but are not limited to, peptide libraries (see, e.g., U.S. Pat. No. 5,010,175, Furka (1991) *Int. J. Pept. Prot. Res.,* 37: 487–493, Houghton et al. (1991) *Nature,* 354: 84–88). Peptide synthesis is by no means the only approach envisioned and intended for use with the present invention. Other chemistries for generating chemical diversity libraries can also be used. Such chemistries include, but are not limited to: peptoids (PCT Publication No. WO 91/19735, Dec. 26, 1991), encoded peptides (PCT Publication WO 93/20242, Oct. 14, 1993), random bio-oligomers (PCT Publication WO 92/00091, Jan. 9, 1992), benzodiazepines (U.S. Pat. No. 5,288,514), diversomers such as hydantoins, benzodiazepines and dipeptides (Hobbs et al., (1993) *Proc. Nat. Acad. Sci. USA* 90: 6909–6913), vinylogous polypeptides (Hagihara et al. (1992) *J. Amer. Chem. Soc.* 114: 6568), nonpeptidal peptidomimetics with a Beta-D-Glucose scaffolding (Hirschmann et al., (1992) *J. Amer. Chem. Soc.* 114: 9217–9218), analogous organic syntheses of small compound libraries (Chen et al. (1994) *J. Amer. Chem. Soc.* 116: 2661), oligocarbamates (Cho, et al., (1993) *Science* 261: 1303), and/or peptidyl phosphonates (Campbell et al., (1994) *J. Org. Chem.* 59: 658). See, generally, Gordon et al., (1994) *J. Med. Chem.* 37:1385, nucleic acid libraries (see, e.g., Strategene, Corp.), peptide nucleic acid libraries (see, e.g., U.S. Pat. No. 5,539,083) antibody libraries (see, e.g., Vaughn et al. (1996) *Nature Biotechnology,* 14(3):

309–314), and PCT/US96/10287), carbohydrate libraries (see, e.g., Liang et al. (1996) Science, 274: 1520–1522, and U.S. Pat. No. 5,593,853), and small organic molecule libraries (see, e.g., benzodiazepines, Baum (1993) C&EN, January 18, page 33, isoprenoids U.S. Pat. No. 5,569,588, thiazolidinones and metathiazanones U.S. Pat. No. 5,549,974, pyrrolidines U.S. Pat. Nos. 5,525,735 and 5,519,134, morpholino compounds U.S. Pat. Nos. 5,506,337, benzodiazepines 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.).

A number of well known robotic systems have also been developed for solution phase chemistries. These systems include automated workstations like the automated synthesis apparatus developed by Takeda Chemical Industries, LTD. (Osaka, Japan) and many robotic systems utilizing robotic arms (Zymate II, Zymark Corporation, Hopkinton, Mass.; Orca, Hewlett-Packard, Palo Alto, Calif.) which mimic the manual synthetic operations performed by a chemist. Any of the above devices are suitable for use with the present invention. The nature and implementation of modifications to these devices (if any) so that they can operate as discussed herein will be apparent to persons skilled in the relevant art. In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

B) High Throughput Assays of Chemical Libraries for Modulators of DPR-1 Expression and/or Activity.

Any of the assays for agents that modulate DPR-1 family receptor expression or activity are amenable to high throughput screening. As described above likely modulators either inhibit expression of the gene product, or inhibit the activity of the receptor. Preferred assays thus detect inhibition of transcription (i.e., inhibition of mRNA production) by the test compound(s), inhibition of protein expression by the test compound(s), binding to the gene (e.g., gDNA, or cDNA) or gene product (e.g., mRNA or expressed protein) by the test compound(s). High throughput assays for the presence, absence, or quantification of particular nucleic acids or protein products are well known to those of skill in the art. Similarly, binding assays are similarly well known. Thus, for example, U.S. Pat. No. 5,559,410 discloses high throughput screening methods for proteins, U.S. Pat. No. 5,585,639 discloses high throughput screening methods for nucleic acid binding (i.e., in arrays), while U.S. Pat. Nos. 5,576,220 and 5,541,061 disclose high throughput methods of screening for ligand/antibody binding.

In addition, high throughput screening systems are commercially available (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These systems typically automate entire procedures including all sample and reagent pipetting, liquid dispensing, timed incubations, and final readings of the microplate in detector(s) appropriate for the assay. These configurable systems provide high throughput and rapid start up as well as a high degree of flexibility and customization. The manufacturers of such systems provide detailed protocols the various high throughput. Thus, for example, Zymark Corp. provides technical bulletins describing screening systems for detecting the modulation of gene transcription, ligand binding, and the like.

VI. Use of DPR-1 Family Receptors to Dissect Signaling Pathways.

C. elegans genetics will be very useful for finding the specific components of the signaling pathway that used by members of this family (the DPR-1 family), including the human homologues, the estrogen receptor related proteins (ERRs). By identifying the components of the signaling pathway, it becomes possible to identify agents (e.g. drugs) that may interfere or enhance this signaling pathway. Drugs that specifically target this pathway and not the classic genomic pathway, may have fewer side effects than the current steroid drugs.

Another possible target for agent interaction is the membrane localization of DPR-1, and, other members of the DPR-1 family. Once again, the fact that DPR-1 is in C. elegans is a distinct advantage over mammalian systems because of the power of C. elegans genetics. Worms can be mutated, and screened using conventional mutagenesis or RNAi methods to identify worms in which DPR-1 mislocalized, or in which the DPR-1 signaling system is altered. The mutated genes responsible for mislocalization or altered signaling can then be identified using well-established molecular genetic techniques. The identified genes provide targets for the identification of pharmacological agents that affect membrane-associated steroid-like signaling pathways.

VII. Use of DPR-1 in Nematode Control.

As the putative dauer pheromone receptor, DPR-1 is useful for development agents that control the reproduction and infectivity of other species of nematodes, which are of agricultural or medical importance. Without being bound to a particular theory, it is believed that DPR-1 and/or its family members are receptors for nematode pheromones. Thus, it is believed that members of this family can be isolated from other nematodes (e.g., parasitic and/or pathogenic) species based on their similarity to the C. elegans family members. This would identify pheromones that trigger alternative (dauer-like) developmental phases for that species, which would lead to identification of the relevant pheromone molecules and of agonists and/or antagonists that affect the activities of the pheromone receptors. Identification of dauer pheromones and receptors would prove beneficial to the exploitation of nematodes that are cultivated as biocontrol agents for insect pests by developing agents that promote the infective dauer-like state in these nematodes.

Thus beneficial nematodes that are currently being cultivated as controlling agents for insect pests can be modified to generate nematodes that are preferentially in the infective state, and thus more effective at killing insect pests. In addition, the infectivity or reproduction of parasitic nematodes could be caused to arrest at the dauer/infective state by application of their specific dauer pheromone (the receptor identified by homology to DPR-1, which would allow identification of the pheromone). By blocking the nematodes in the dauer/infective state, no reproduction would occur, and the population would die out. Alternatively, antagonists of the receptor might be used to prevent nematodes from entering an invasion-competent, or a resistant state, thereby preventing them from productive invasion.

VIII. DPR-1 in Expression Systems.

In certain embodiments, this invention provides novel kits and expression systems. One system and kit takes advantage of the classic function of DPR-1, i.e., DPR-1 acting (as other NHRs do) as a ligand-inducible transcriptional regulator. DPR-1 can be used to generate an inducible protein system (similar to the ecdysone kit in use today). The protein of interest is cloned downstream of DPR-1 binding sites, and this construct along with a DPR-1 expression construct is transfected into tissue culture cells. On addition of dauer pheromone, DPR-1 would bind DNA and activate transcription of the protein of interest. Because tissue culture cells do not contain dauer pheromone, the researcher would be able to turn the gene on and off without interference from endogenous ligands.

In addition to the inducible promoter system, DPR-1 could also be used to generate a system and a kit useful for targeting proteins to the membrane or subjecting it to regulation by a steroid-like molecule at the cell surface. By including the amino acids from DPR-1 necessary for its localization to the membrane, one can generate a "tag" that can be placed on other proteins, targeting them to the membrane and making them responsive to a selected ligand, by including the appropriate ligand binding domain of an NHR. Such a system would be useful for researchers studying signal transduction, cell surface markers or other applications.

Other Uses of DPR-1 Family Members.

Components of the dauer pathway affect lifespan of *C. elegans*. Dauer larva live many times longer than normal adult *C. elegan*. In addition, certain mutations in the dauer-induction pathway can greatly extend the life of adult animals. DPR-1 as a putative dauer pheromone receptor, reveals the initiating step that regulates the animal's lifespan, which could provide methods for identifying agents that extend lifespan in other animals or humans.

EXAMPLES

The following examples are offered to illustrate, but not to limit the claimed invention.

Example 1

Analysis of DPR-1

FIG. 1 illustrates similarities of DPR-1 and other NHRs. DPR-1 encodes a nuclear hormone receptor (NHR) as determined by its sequence similarity to other NHRs. DPR-1 defines a family of NHRs in *C. elegans* (two members, C54C8 and Y38E10, of which are shown). In addition, similarity to the human estrogen receptor related (ERR) gamma and beta proteins, the human mineralocorticoid receptor and the human progesterone receptor are also shown. Of all the non-*C. elegans* proteins, DPR-1 is most similar to the human ERR genes, suggesting that the ERRs are the human equivalent of DPR-1.

DPR-1 (formerly END-2) has been designated R10D12.2 by the *C. elegans* sequencing consortium. We have found the predicted sequence of DPR-1 (R10D12.2) as reported in the database is incorrect. Although we detect an mRNA product by RT-PCR using primers for the predicted start site of 9649 and the predicted stop site (position 7577), our sequence analysis shows that a different splice site from that predicted by Genefinder is used, leading to a premature stop codon. The splice predicted by Genefinder is at position 9519, but the actual spice site is at 9544, based on analysis of the RT-PCR product. The RT product predicts a premature stop codon at nucleotide position 9436, if the same start codon predicted by Genefinder is used. A downstream start codon at position 9563 is present in a different reading frame from the Genefinder predicted site. Given utilization of the splice site at position 9544, this start codon generates a full-length predicted protein beyond this site. There are three other differences from the reported sequence: an additional intron, as well as two changes in amino acids. The additional intron is at positions 7675 to 7630. In addition, our sequence shows that there is a C instead of a T at position 7969, leading to a change of leucine to proline in the predicted protein, and a G instead of an A at position 8495, leading to a change of a methionine to a valine in the protein.

At least 20 other members of the DPR-1 family in *C. elegans* (based on similarity within the DNA binding and ligand binding domain) include NHRs on the following cosmids: C54C8, ZK381, F41D3, C27C7, ZK1025, C14C6, C17A2, F14A5, C49D10, T15D6, C47F8, C29G2, E03H4, and the following genes, nhr-20, nhr-53, nhr-16, and nhr-92. Family members determined by analysis of the DNA binding domain (done by Ann Sluder, personal communication) are as follows: C54C8.1, C41G6.5, F41D3.3, C29G2.5, C47F8.2, E03H4.6, T09E11.2, nhr-20 and nhr-77.

FIG. 2 illustrates DPR-1 expression in embryos. Maternal DPR-1 expression is detectable by in situ hybridization of transcripts throughout very early embryos (shown are 2-cell and 4-cell embryos) with a higher concentration in the posterior of the embryo, in the P lineage ($P_1$ and $P_2$ cells). Zygotic transcription is detectable from the bean stage (although it presumably occurs earlier, since transgene transcription is detectable from the E4 stage). Zygotic mRNA is present at high levels in the gut (the endoderm lineage), with lower levels present in the pharynx (ph; comma and pretzel stages are shown). β-galactosidase and GFP (not shown) expression from reporter constructs is also observed within the endoderm lineage. These reporter transgenes contain DPR-1 promoter sequences with approximately 30 amino acids of DPR-1 fused to β-galactosidase and GFP, and contain a nuclear localization signal. Transgene expression is first detectable at the E4 stage (not shown).

As shown in FIG. 3, DPR-1 antibody is specific for DPR-1. To test the specificity of the DPR-1 antibody, pre-immune serum was used in place of the DPR-1 antibody, and no staining was observed (FIG. 3A). The larva were permeabilized, as shown by the staining of a control antibody, 1CB4, which, like DPR-1, stains endodermal cells (FIG. 3B). DPR-1 was not detected in embryos carrying a deletion (itDf2) of the genomic region containing DPR-1. itDf2 embryos do not make endoderm. To confirm that the DPR-1 antibody does not detect an unrelated endoderm-specific antigen, we rescued endoderm development in itDf2 animals using end-1. These embryos contain endoderm, as revealed by the presence of gut-specific granules and the antigen detected by antibody MH33 (FIG. 3D), yet DPR-1 is not detected (FIG. 3C).

DPR-1 antibodies were generated with the following peptides: *end2-1, *end2-2, and *end2-3. The N terminal end2-1 peptide was picked based on the Genefinder predicted sequence of DPR-1. After cloning the cDNA, we discovered that the predicted initiation ATG was not correct. The result was that the DPR-1-1 peptide is not actually contained within DPR-1. However, DPR-1 antibody affinity purified against only DPR-1-3 produced the same result as that purified against all three peptides. The peptides were prepared by Gibco BRL, and a portion were conjugated to KLH, and injected into rabbits, that had been prescreened for an absence of serum cross-reactivity to *C. elegans* proteins (by immunocytochemistry). Rabbits were injected and housed by Cocalico. Serum was affinity purified using the AmminoLink kit (Pierce).

FIG. 4 shows that DPR-1 is nuclear in early embryos. In early embryos (pre-bean), DPR-1 is detected in the nucleus. FIG. 4, panel A shows DPR-1 antibody staining of an approximately 16-cell embryo. DPR-1 is present in posterior nuclei of the embryo. FIG. 4, panel B shows detection of P granules using OICID4 antibody to mark the posterior of the embryo.

Figure 5:
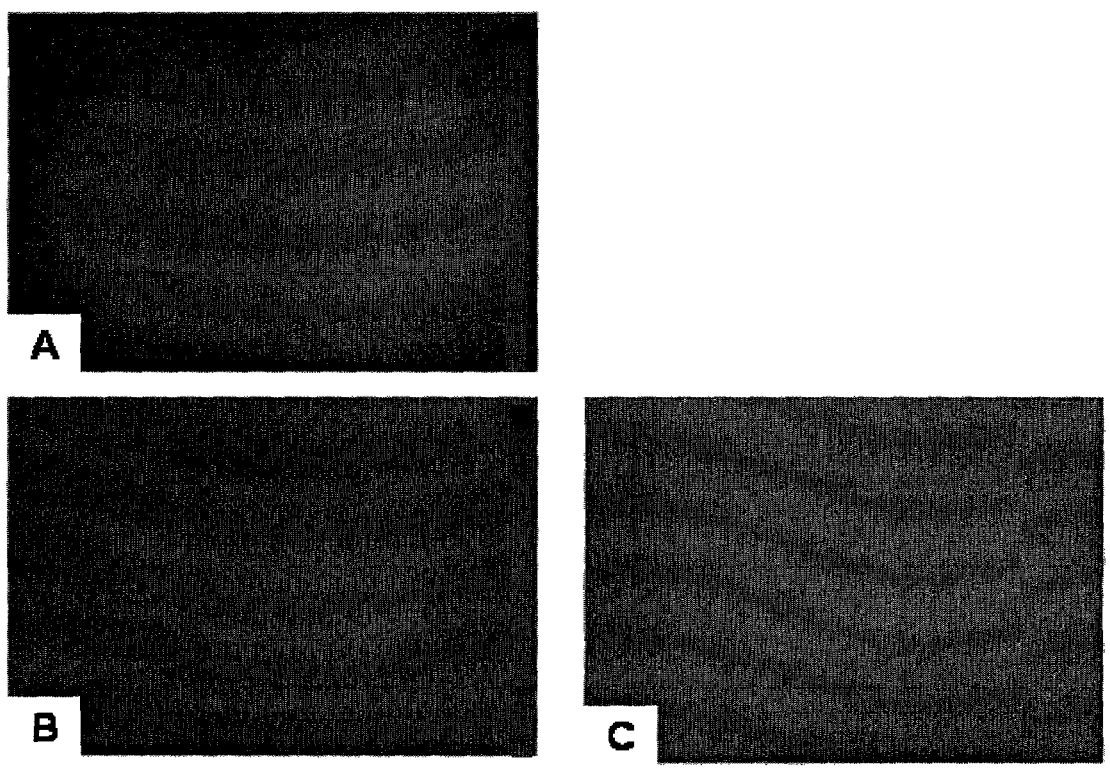
FIG. 5 shows that ectopically expressed DPR-1 is localized to the cell surface. Panels A–C show three different examples of embryos ectopically expressing DPR-1 using the heat shock promoter.

FIG. 5 shows that DPR-1 localizes to the membrane in later embryos. Detection of DPR-1 in mixed-stage embryos. E16 (16 E cells present, about 200 cells), E20 (20 E cells present, about 300 cells) and comma stage embryos (about 300 cells) show DPR-1 staining around the perimeter of endodermal cells. In embryos, there is a clear demarcation of the cell boundaries (contrast to DPR-1 staining in larva), similar to what is seen in dauer pheromone-treated larvae. Note that in some embryos at the E16 stage, DPR-1 is present in the apical and lateral membranes, and excluded from the basal membrane, while at later stages, DPR-1 is present around the entire cell.

Methods

Embryos were collected by hypochlorite treatment of gravid adults. Embryos were placed on poly-lysine coated slides, freeze-cracked and fixed in methanol/acetone. The DPR-1 antibody was affinity purified, diluted 1:5 in 10% goat serum and applied to the sample overnight at 4° C. After extensive washing, FITC-labeled, goat anti-rabbit antibody was used to detect DPR-1.

FIG. 6 shows that ectopically expressed DPR-1 is localized to the cell surface. DPR-1 was expressed throughout the embryo by inserting genomic DPR-1 downstream of a heat-shock promoter, generating transgenic lines, and incubating the worms at 34° C. for 45 minutes. Immunocytochemistry using DPR-1 antibody reveals that DPR-1 is present throughout the embryos, and is membrane localized.

FIG. 7 shows that DPR-1 is not localized to the nucleus, but is present in the membrane or cytoplasm. DPR-1 is localized to the cytoplasm or the membrane (shown in red), but not in the nucleus. The nucleus is marked with elt-2:GFP (shown in green). ELT-2 is a transcription factor that is present in the gut nuclei.

FIG. 8 shows that DPR-1 is localized to the basal membrane in larvae. DPR-1 does not colocalize with the antigen recognized by antibody MH33 in larvae. MH33 recognizes an antigen in the brush border of the intestine, and outlines the apical side of the intestinal epithelial cells. DPR-1 is detected in the basal membrane, and does not overlap with MH33 staining.

FIG. 9 shows that DPR-1 moves from the cytoplasm to the membrane when worms are crowded. FIGS. 9A and 9B: DPR-1 is detectable in the cytoplasm of L1s grown in uncrowded conditions. Note that there staining is excluded from the nucleus. FIG. 9B shows a close-up view of the area boxed in FIG. 9A. When L1 larvae are crowded, DPR-1 is detectable at the membrane. FIG. 9D shows a close-up view of the area boxed in FIG. 9C. Arrows point to the approximate location of nuclei.

Figure 10:
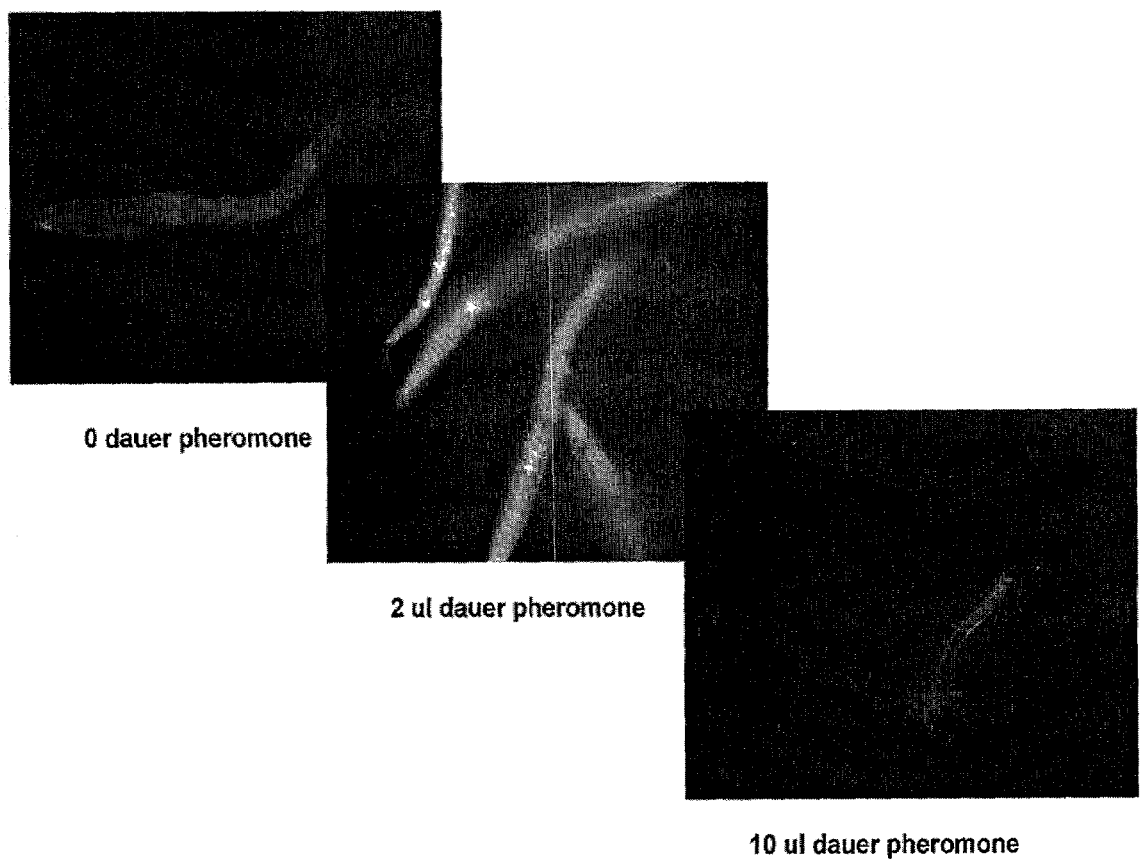
FIG. 10 illustrates the graded response of DPR-1 to dauer pheromone levels. Immunoreactive DPR-1 shows varying association with the membrane at different levels of exposure to dauer pheromone. Assays were performed as described herein.

FIG. 10 shows that DPR-1 moves to the membrane in response to dauer pheromone. FIGS. 10A and 10B: L1 larvae grown in non-crowded conditions show DPR-1 localization in the cytoplasm. FIGS. 10C and 10D: In the presence of dauer pheromone, DPR-1 localizes to the membrane. Note that this membrane localization is different from that seen in crowded worms in that the lateral surfaces of the cells show strong DPR-1 staining. FIGS. 10B and 10D are close-ups of the areas boxed in A and C respectively. Arrows point to the approximate location of nuclei. Assays were done in 400 µl of M9 buffer with continuous aeration at room temperature, for approximately 16 hours. Worms were then harvested for staining.

Figure 11:
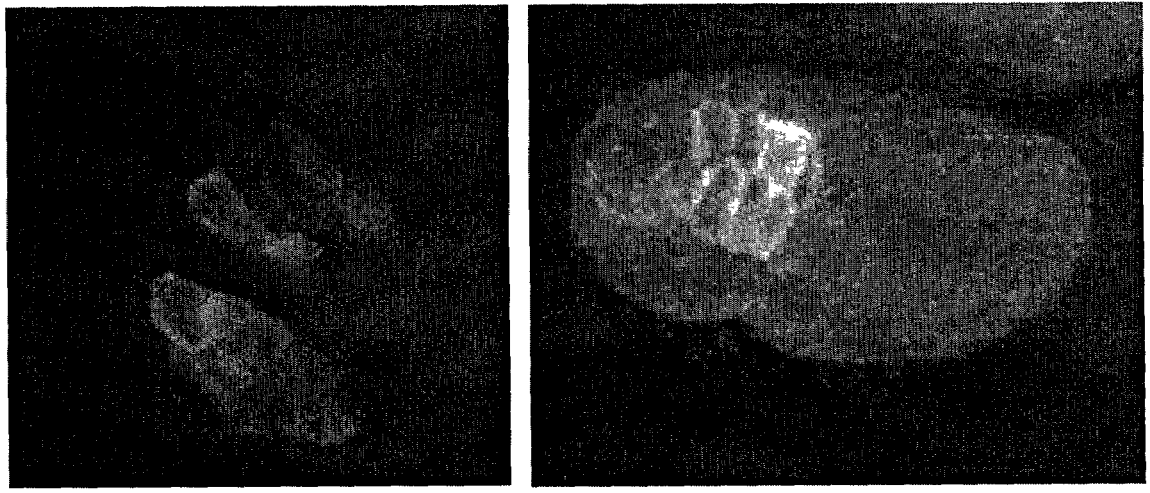
FIG. 11 shows that myc tagged DPR-1 is at the membrane in embryos as is endogenous DPR-1. Left panel: α-MYC aby; Right panel: αDPR-1 aby.

FIG. 11 illustrates the graded response of DPR-1 to dauer pheromone levels. Immunoreactive DPR-1 shows varying association with the membrane at different levels of exposure to dauer pheromone. Assays were performed as described in FIG. 10. In the absence of pheromone, it is cytoplasmic and nuclear excluded. At an intermediate levels (2 µl), the staining is clearly located at the membrane, with signal clearly discerned at the margins between cells (i.e., lateral faces of the membranes). At high levels (10 µl), the staining becomes punctate and does not show signal between cells, perhaps indicating no association with the lateral membranes. These observations demonstrate that DPR-1 responds to dauer pheromone in graded manner.

Example 2

Further Analysis of DPR-1

DPR-1 Localization.

In order to confirm our antibody staining, we generated transgenic worms (*C. elegans*) carrying a construct of DPR-1 containing a myc tag. We were then able to use an antibody to myc to detect the localization of the fusion protein. We found that the localization of the transgenic DPR-1 was similar to the localization of the endogenous DPR-1 detected by our antibody. myc::DPR-1 was detected in the cytoplasm and membrane at all stages of development. In addition to the cytoplasmic and membrane staining, we also detected myc staining in the nucleus. This may be an artifact due to overexpression of the transgenic protein, or may be caused by the myc moiety, which, though small, may be interfering with the proper localization of the protein. It is also possible that endogenous DPR-1 is in the nucleus, but the epitope recognized by our antibody is somehow occluded. In any case, myc::DPR-1 is detectable at the membrane, as we have seen for endogenous DPR-1.

DPR-1 Localization Changes in Response to Dauer Pheromone Dose.

Figure 12:
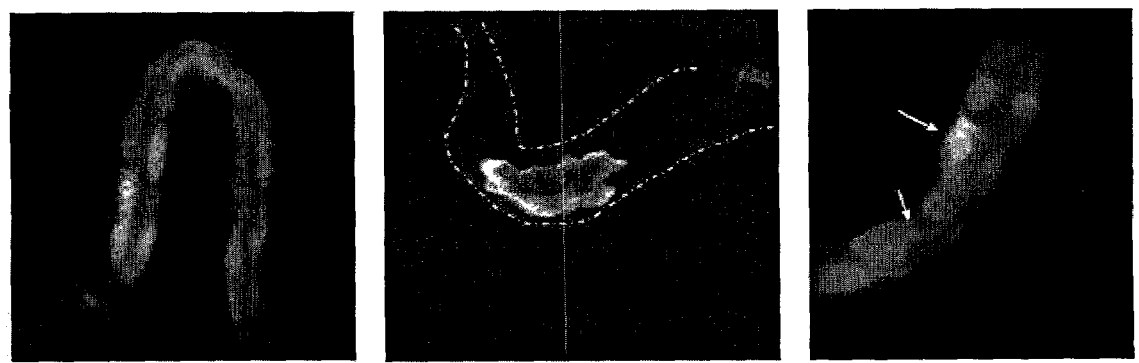
FIG. 12 shows that mc tagged DPR-1 behaves like endogenous DPR-1. Left panel: non-crowded; Middle panel: crowded; Right panel: +dauer pheromone.

The dauer pheromone causes a change in localization of DPR-1 from the cytoplasm to the membrane. The localization of DPR-1 in the presence of Dauer pheromone was different than the localization of DPR-1 in crowded worms (compare FIGS. 12 and 13). DPR-1 localization in the presence of dauer pheromone is reminiscent of its localization in embryos, in that it outlines the cells in the gut. When worms are treated with 10 fold higher concentration of dauer pheromone, a new localization pattern appears. DPR-1 is localized to the apical boundary of the intestine.

Biochemical Analysis of DPR-1 Localization.

Figure 13A:
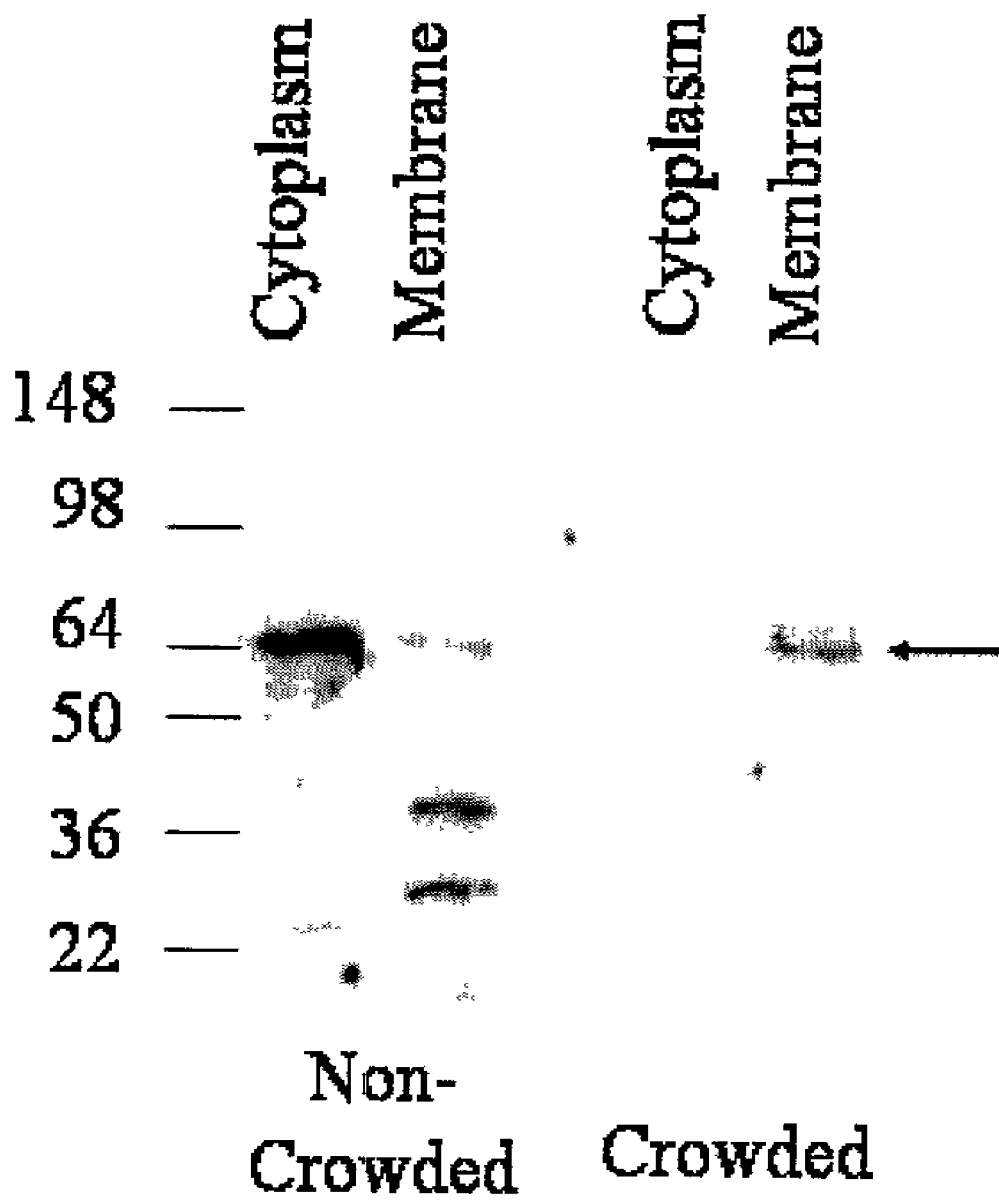
FIGS. 13A and 13B show a biochemical analysis of DPR-1 localization.
Figure 13B:
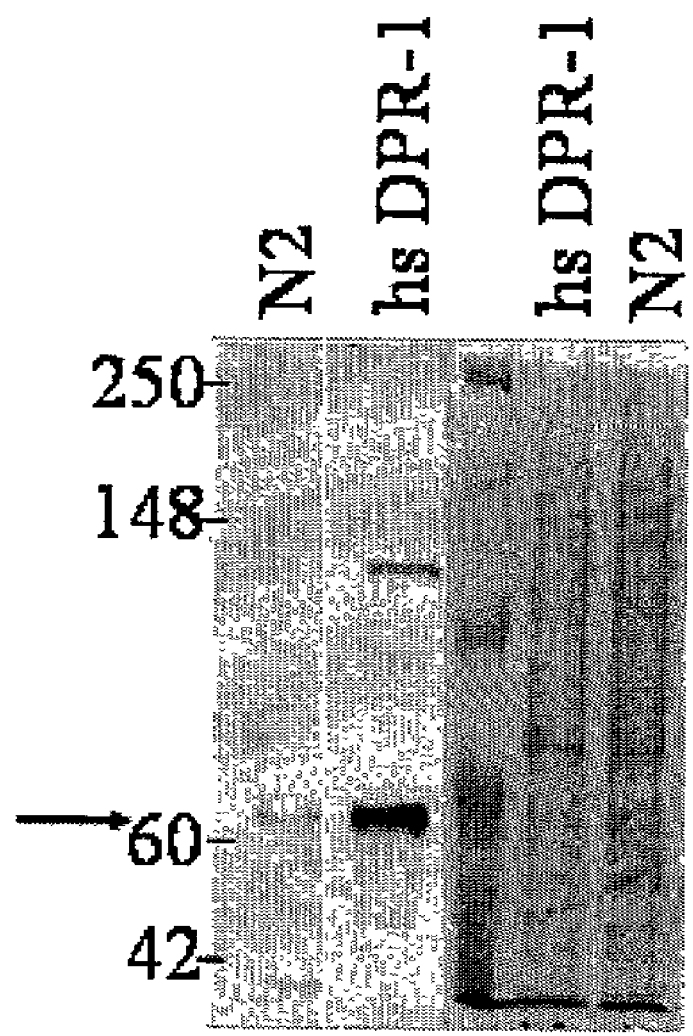

To further understand the localization of DPR-1, we undertook a biochemical approach. We obtained cytoplasmic and membrane fractionated extracts of worms grown under different conditions and analyzed the localization of DPR-1 using western blots. The results obtained with the biochemical approach confirm our antibody staining. Extracts of worms grown in non-crowded conditions contain DPR-1 in the cytoplasmic fraction, with little in the membrane fraction. When worms are grown in crowded conditions, DPR-1 is localized to the membrane fraction (FIG. 13). To demonstrate that the antibody is recognizing DPR-1, we prepared extracts from worms overexpressing DPR-1 under control of the heat shock promoter, and probed with the DPR-1 antibody. As expected, we obtained a more abundant band at the same molecular weight when DPR-1 was overexpressed. Taken together, these data confirm the immunocytochemisty localization of DPR-1.

Figure 14:
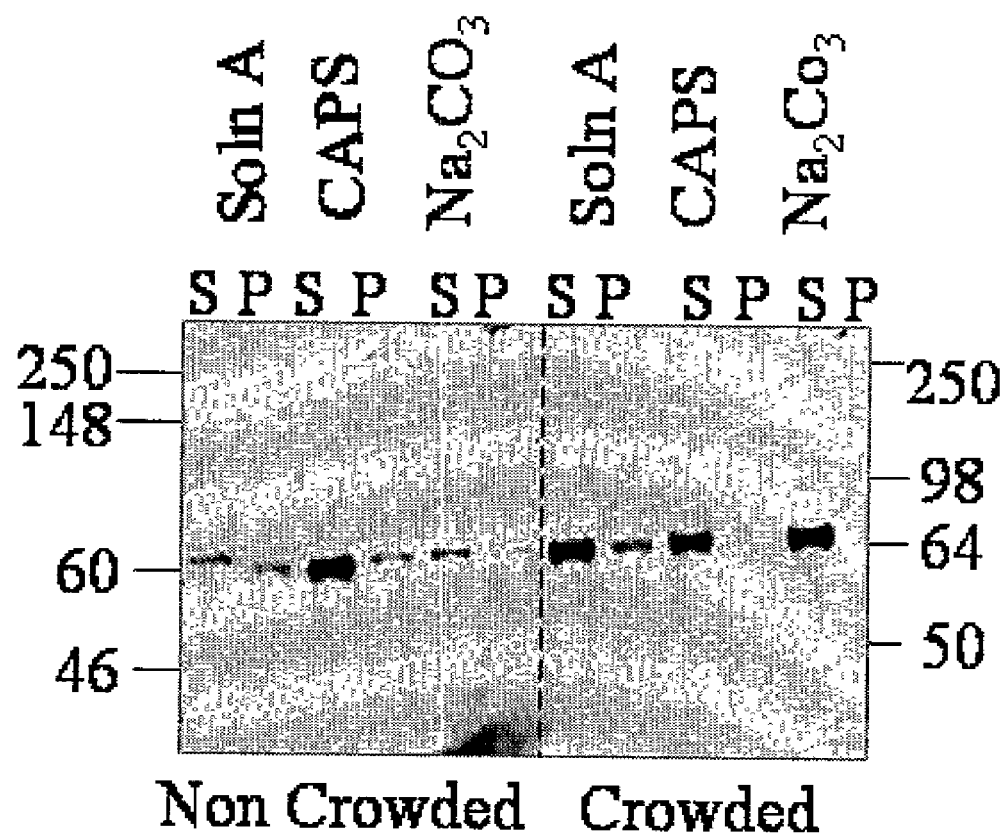
FIG. 14 shows that DPR-1 is a peripheral membrane protein.
Figure 15A:
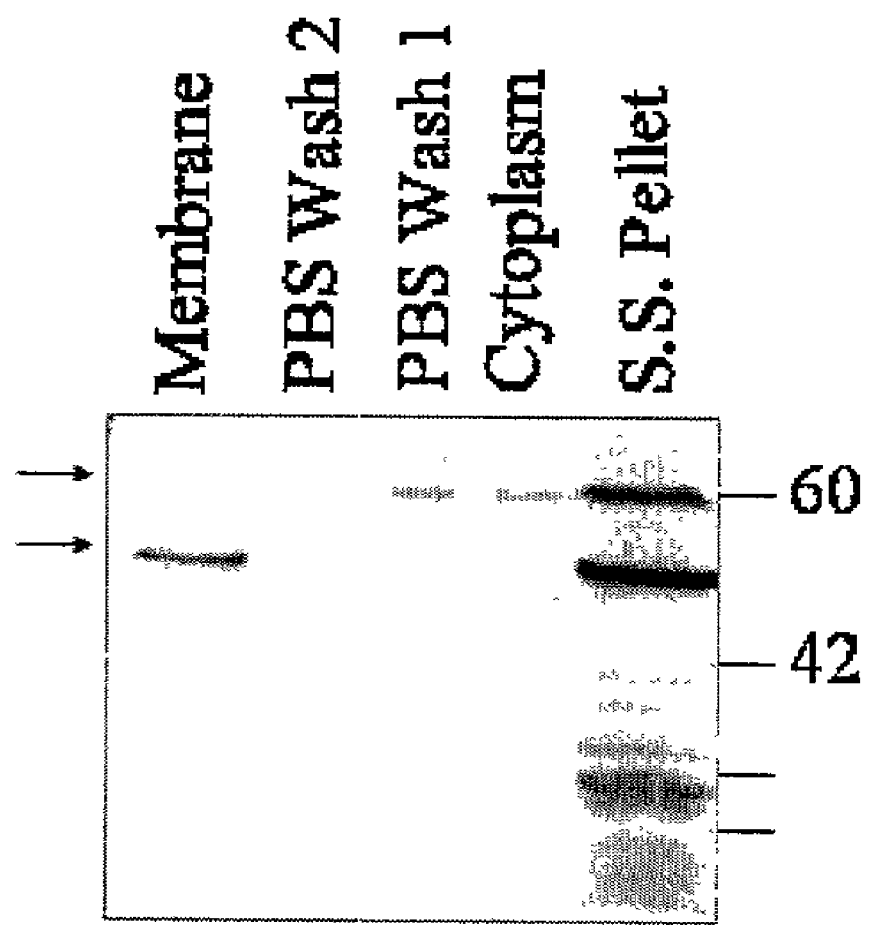
FIGS. 15A and 15B show that two forms of DPR-1 exist in dauers
Figure 15B:
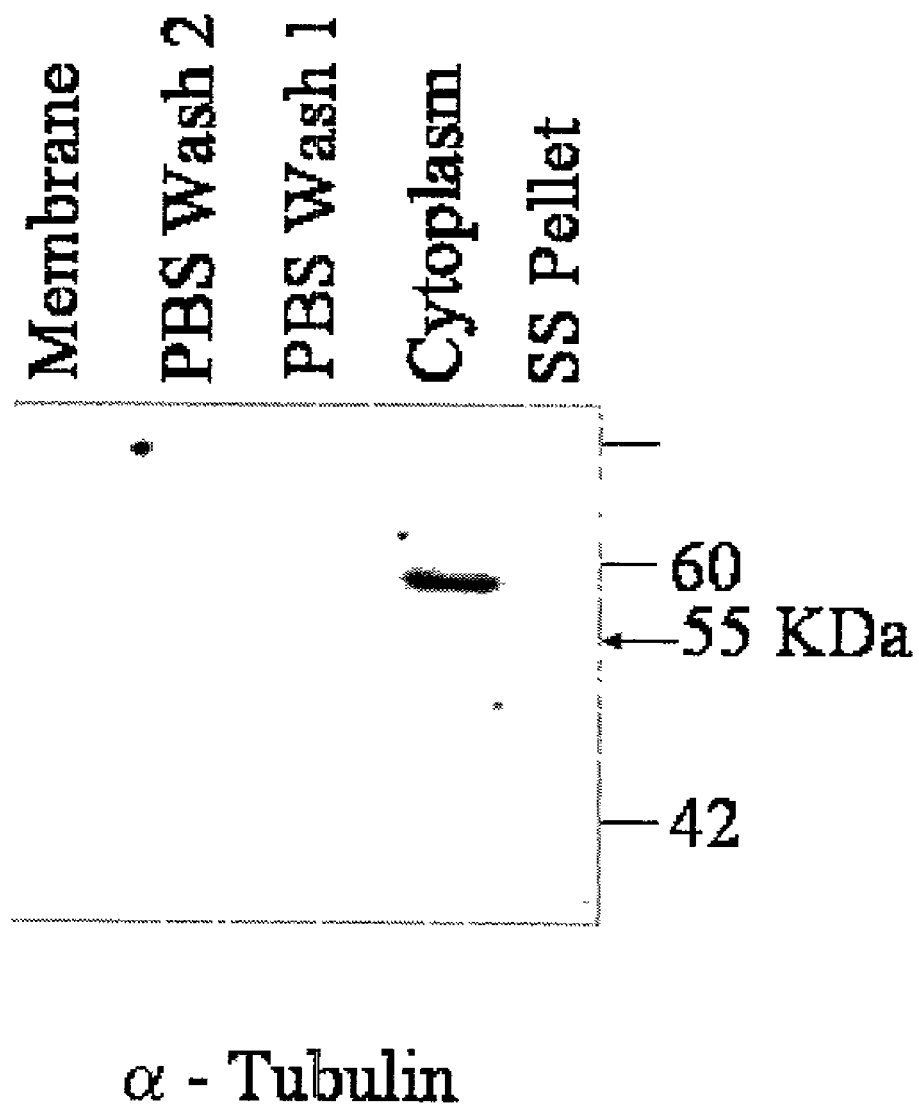
Figure 16A:
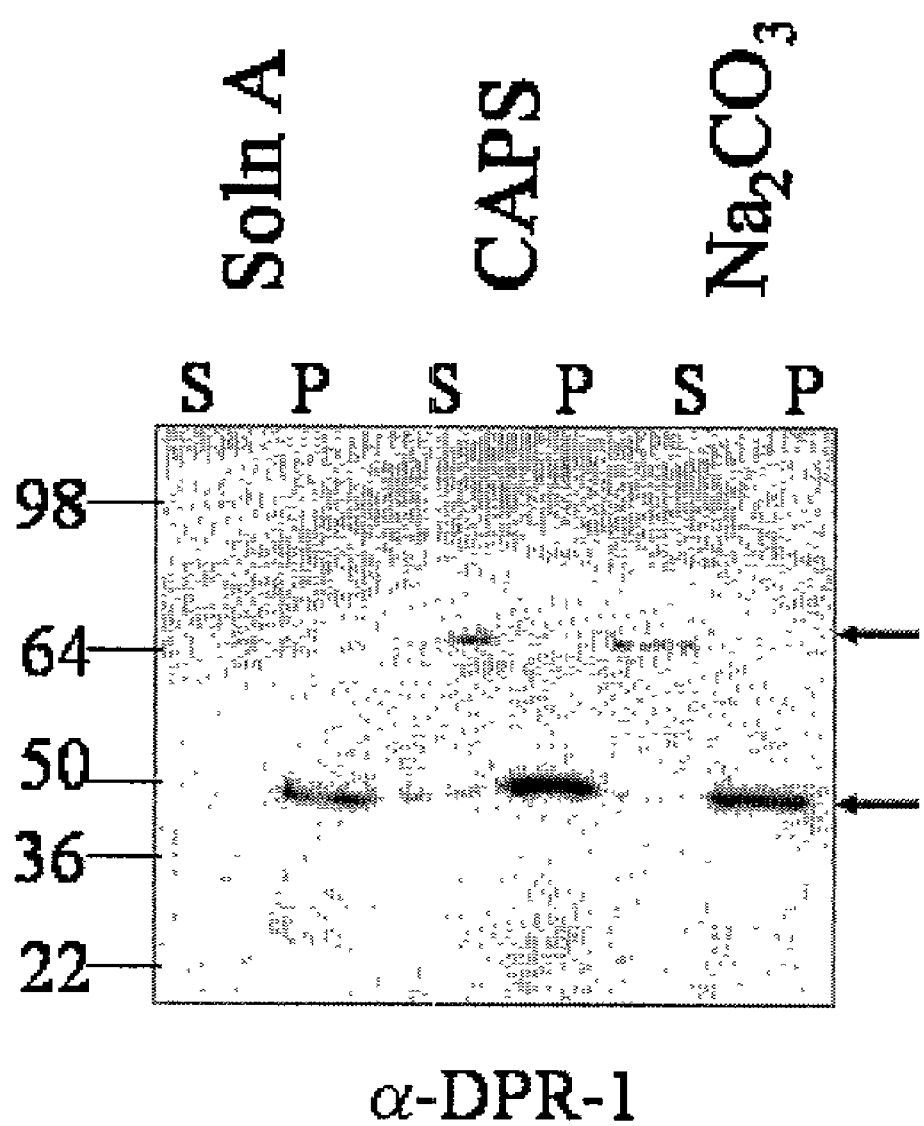
FIGS. 16A and 16B show that the smaller form of DPR-1 in dauers is an integral membrane protein.
Figure 16B:
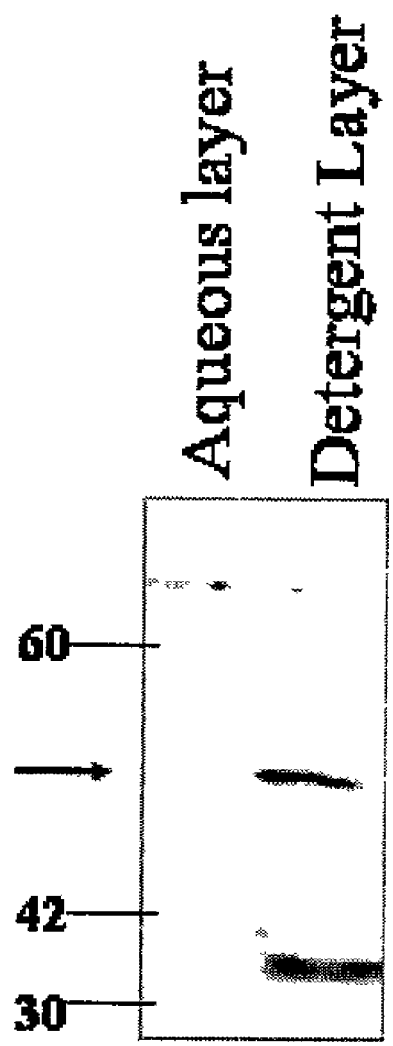

We next wanted to determine whether DPR-1 was an integral or peripheral membrane protein when it is localized to the membrane. We used several different methods that would remove DPR-1 from the membrane if it was a peripheral protein, and found that it was indeed a peripheral protein (FIG. 14). Interestingly, in dauers, there appears to be an alternative form of DPR-1 (FIG. 15) that is smaller than the form found in non-dauers and appears to be an integral membrane protein (FIGS. 16A and B).

Figure 17:
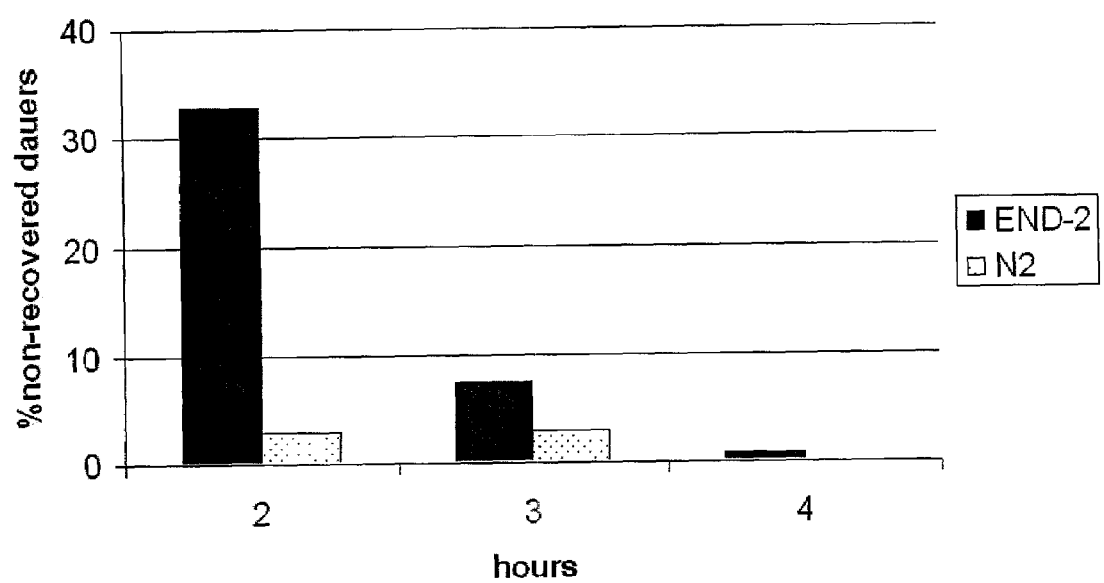
FIG. 17 shows that DPR-1 (END-2) prevents dauer recovery.

Functional Data of DPR-1:

The change in localization of DPR-1 in the presence of dauer pheromone suggests a role for DPR-1 in dauer development. We analyzed dauer formation and recovery in worms that overexpress DPR-1. The worms were allowed to starve to form dauers, and the rate at which they recover in the presence of food was measured. Worms carrying the DPR-1 transgene were significantly slower at recovering from dauer than wildtype worms, or worms carrying a control transgene (FIG. 17). In addition, from 3 different lines of worms carrying the DPR-1 transgene, more than 38 dauers did not recover after 24 hours (wildtype dauers recover in 12 hours), 25 of these had not recovered in 48 hours, and 4 did not recover even 1 week later. These results strongly suggest that overexpressing DPR-1 prevents timely dauer recovery.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of screening for an agent that modulates dauer formation by a nematode, said method comprising: contacting a nematode with a test agent; and detecting a change in localization of a nuclear hormone receptor, said nuclear hormone receptor characterized by a DNA binding domain and a corresponding ligand binding domain as set forth in an amino acid selected form the group consisting of DPR-1 polypeptide of SEQ ID NO:15; or C54C8 comprising SEQ ID NOs:2 and 9; or Y38E10 comprising SEQ ID NOs:3 and 10 wherein a change in localization indicates that said test agent is a good candidate agent modulating dauer formation by a nematode.

2. The method of claim 1, wherein said change in localization is a change from localization in the cell nucleus to localization in the cell membrane.

3. The method of claim 1, wherein said change in localization is detected by labeling said nuclear receptor hormone.

4. The method of claim 1 wherein said nuclear hormone receptor is DPR-1.

5. A method for identifying a compound which binds to a DPR-1 nuclear hormone receptor which can locate to a plasma membrane, the method including:

a. bringing into contact (i) a nuclear hormone receptor polypeptide having a DNA binding domain and a corresponding ligand binding domain, said polypeptide having a sequence selected for the group consisting of DPR-1 polypeptide of SEQ ID NO:15; or C54C8 comprising SEQ ID NOs:2 and 9; or Y38E10 comprising SEQ ID NOs:3 and 10

With (ii) a test compound, under conditions wherein said nuclear hormone receptor polypeptide and said test compound will bind; and b. determining binding between said nuclear hormone receptor polypeptide and said test compound.

6. The method of claim 5 wherein said DPR-1 polypeptide is expressed in a cell and located on a cell membrane.

7. The method of claim 5 wherein said DPR-1 polypeptide is a polypeptide of SEQ ID NO:15.

8. The method of claim 5 wherein said DPR-1 polypeptide is expressed in a cell by a transgene coding for said DPR-1 polypeptide.

9. The method of claim 5 wherein said transgene comprises a sequence of SEQ ID NO: 16.

10. The method of claim 5 wherein said determining step comprises a method selected from the group consisting of capillary electrophoresis, a Western blot, mass spectroscopy, ELISA, immunochromatography, and immunohistochemistry.

11. A method for identifying a compound which binds to a DPR-1 nuclear hormone receptor which can locate to a plasma membrane, the method including:
 a. bringing into contact
  (i) a cell expressing a nuclear hormone receptor polypeptide having a DNA binding domain and a corresponding ligand binding domain, said polypeptide having a sequence selected for the group consisting of:
  DPR-1 polypeptide of SEQ ID NO:15; or
  C54C8 comprising SEQ ID NOs:2 and 9; or
  Y38E10 comprising SEQ ID NOs:3 and 10; with
  (ii) a test compound, under conditions wherein said DPR-1 nuclear hormone receptor and said test compound will bind; and
 b. determining binding between said nuclear hormone receptor polypeptide and said test compound.

12. The method of claim 11 wherein said cell is a *C. elegans* cell.

13. The method of claim 12 wherein the cell is in a *C. elegans* animal.

14. The method of claim 11 wherein said cell is an oocyte.

15. The method of claim 11 wherein said cell is cultured ex vivo.

16. The method of claim 12 wherein step a (ii) further comprises the step of contacting the cell with dauer pheromone.

17. The method of claim 11 wherein said DPR-1 polypeptide is a polypeptide of SEQ ID NO:15.

18. The method of claim 11 wherein said cell expresses a transgene encoding said nuclear hormone receptor.

19. The method of claim 18 wherein said transgene is linked to a reporter gene.

20. The method of claim 11 wherein said determining step comprises a method selected from the group consisting of a Northern blot, a Southern blot using DNA derived from an DPR-1 RNA, an array hybridization, an affinity chromatography, and an in situ hybridization.

21. The method of claim 11 wherein said test compound is a nucleic acid.

* * * * *